United States Patent [19]
Riedl et al.

[11] Patent Number: 5,843,967
[45] Date of Patent: *Dec. 1, 1998

[54] 6-MEMBERED NITROGEN-CONTAINING HETEROARYL-OXAZOLIDINONES

[75] Inventors: Bernd Riedl; Dieter Häbich; Andreas Stolle, all of Wuppertal, Germany; Hanno Wild, Orange, Conn.; Rainer Endermann, Wuppertal, Germany; Klaus Dieter Bremm, Recklinghausen, Germany; Hein-Peter Kroll, Wuppertal, Germany; Harald Labischinski, Wuppertal, Germany; Klaus Schaller, Wuppertal, Germany; Hans-Otto Werling, Wuppertal, Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[ * ] Notice: The term of this patent shall not extend beyond the expiration date of Pat. No. 5,627,181.

[21] Appl. No.: 749,581

[22] Filed: Nov. 15, 1996

Related U.S. Application Data

[63] Continuation of Ser. No. 503,369, Jul. 17, 1995, Pat. No. 5,627,181.

[30] Foreign Application Priority Data

Jul. 20, 1994 [DE] Germany .......... 44 25 612.4

[51] Int. Cl.⁶ .......... A61K 31/44; C07D 401/04
[52] U.S. Cl. .......... 514/340; 514/333; 546/256; 546/271.4
[58] Field of Search .......... 546/271.4, 256; 514/340

[56] References Cited

U.S. PATENT DOCUMENTS

| | | |
|---|---|---|
| 4,705,799 | 11/1987 | Gregory . |
| 4,801,600 | 1/1989 | Wang et al. . |
| 4,921,869 | 5/1990 | Wang et al. . |
| 4,965,268 | 10/1990 | Wang et al. . |
| 5,254,577 | 10/1993 | Carlson et al. . |
| 5,627,181 | 5/1997 | Riedl et al. .......... 514/236.8 |

FOREIGN PATENT DOCUMENTS

| | | |
|---|---|---|
| 0 311 090 | 4/1989 | European Pat. Off. . |
| 0 312 000 | 4/1989 | European Pat. Off. . |
| 0 352 781 | 1/1990 | European Pat. Off. . |
| 0 359 418 | 3/1990 | European Pat. Off. . |
| 0 605 729 | 7/1994 | European Pat. Off. . |
| 9 309 108 | 5/1993 | WIPO . |
| 9 323 384 | 11/1993 | WIPO . |

OTHER PUBLICATIONS

Borgulya, et al, Chemical Abstracts, vol. 23, (1995) No. 340097g.

C–H. Park, et al., J. Med. Chem., vol. 35, No. 6, pp. 1156–1165, (1992).

I.T. Harrison, et al., "Compendium of Organic Synthetic Methods", vol. 1 and 2, Wiley–Interscience, N.Y. (1971).

*Primary Examiner*—Robert W. Ramsuer
*Attorney, Agent, or Firm*—Sprung Kramer Schaefer & Briscoe

[57] ABSTRACT

The invention relates to 6-membered nitrogen-containing heteroaryloxazolidinones, processes for their preparation and their use as medicaments, in particular as antibacterial medicaments.

17 Claims, No Drawings

6-MEMBERED NITROGEN-CONTAINING HETEROARYL-OXAZOLIDINONES

This is a continuation of application Ser. No. 08/503,369, filed on Jul. 17, 1995, now U.S. Pat. No. 5,627,181.

The present invention relates to 6-membered nitrogen-containing heteroaryloxazolidinones, processes for their preparation and their use as medicaments, in particular as antibacterial medicaments.

N-aryloxazolidinones hazing an antibacterial action are known from the publications U.S. Pat. No. 5,254,577, U.S. Pat. No. 4,705,799, EP 311 090, U.S. Pat. No. 4,801,600, U.S. Pat. No. 4,921,869, U.S. Pat. No. 4,965,268, EP 312 000 and C. H. Park et al., J. Med. Chem. 35, 1156 (1992).

Compounds of the general formula (I) (D=pyridyl and $R^1$=hydroxyl), moreover, are included in a general intermediate product formula in PCT WO 93/22298, neither concrete representatives of these substances nor a pharmacological action being described there.

The present invention relates to 6-membered nitrogen-containing heteroaryloxazolidinones of the general formula (I)

in which $R^1$ represents azido or hydroxyl, or represents a group of the formula $-OR^2$, $-O-SO_2R^3$ or $-NR^4R^5$, wherein $R^2$ denotes straight-chain or branched acyl having up to 8 carbon atoms or a hydroxyl-protective group, $R^3$ denotes straight-chain or branched alkyl having up to 4 carbon atoms or phenyl, which is optionally substituted by straight-chain or branched alkyl having up to 4 carbon atoms, $R^4$ and $R^5$ are identical or different and cycloalkyl having 3 to 6 carbon atoms, hydrogen, phenyl or straight-chain or branched alkyl having up to 8 carbon atoms or an amino-protective group, or $R^4$ or $R^4$ denotes a group of the formula $-CO-R^6$, wherein $R^6$ denotes cycloalkyl having 3 to 6 carbon atoms, straight-chain or branched alkyl having up to 8 carbon atoms, phenyl or hydrogen, D represents a 6-membered aromatic heterocyclic radical which has at least one nitrogen atom and is bonded directly via a carbon atom, or represents a bi- or tricyclic aromatic radical which has at least one nitrogen-containing ring, is bonded directly via a carbon atom and is in each case 6-membered, or represents β-carbolin-3-yl, or represents indolizinyl bonded directly via the 6-membered ring, wherein the cyclic radicals are optionally substituted in each case up to 3 times in an identical or different manner by carboxyl, halogen, cyano, mercapto, formyl, trifluoromethyl, nitro, straight-chain or branched alkoxy, alkoxycarbonyl, alkylthio or acyl having in each case up to 6 carbon atoms or by straight-chain or branched alkyl having up to 6 carbon atoms, which can in turn be substituted by hydroxyl, by straight-chain or branched alkoxy or acyl having up to 5 carbon atoms or by a group of the formula $-NR^7R^8$, wherein $R^7$ and $R^8$ are identical or different and denote hydrogen, formyl, straight-chain or branched alkyl or acyl having in each case up to 4 carbon atoms, phenyl or cycloalkyl having 3 to 6 carbon atoms, or together Filth the nitrogen atom form a 5- to 6-membered saturated heterocyclic radical which optionally has a further hetero atom from the series consisting of N, S and/or O and can in turn be optionally substituted including on a further nitrogen atom, by phenyl, pyrimidyl or straight-chain or branched alkyl or acyl having in each case up to 3 carbon atoms, and/or the cyclic radicals are optionally substituted by a group of the formula $-NR^{7'}R^{8'}$, wherein $R^{7'}$ and $R^{8'}$ are identical or different and have the above-mentioned meaning of $R^7$ and $R^8$ and are identical to or different from these, and/or the cyclic radicals are optionally substituted by ($C_2$–$C_8$)-alkenylphenyl, phenyl or by a 5- or 6-membered saturated or unsaturated heterocylic radical having up to 3 hetero atoms from the series consisting of S, N and/or O, which are in turn optionally substituted by a group of the formula $-CO-NR^9R^{10}$, $-NR^{11}R^{12}$, $-NR^{13}-SO_2-R^{14}$, $R^{15}R^{16}N-SO_2-$, $R^{17}-S(O)_a-$, $R^{18}-N=CH-$ or by the radical $-CH(OH)-SO_3R^{20}$, wherein $a$ denotes a number 0, 1 or 2, $R^9$, $R^{10}$, $R^{13}$, $R^{15}$ and $R^{16}$ are identical or different and denote hydrogen, straight-chain or branched alkyl having up to 6 carbon atoms, tolyl or phenyl, $R^{11}$ and $R^{12}$ are identical or different and have the abovementioned meaning of $R^7$ and $R^8$ and are identical to or different from these.

$R^{14}$ and $R^{17}$ are identical or different and have the abovementioned meaning of $R^3$ and are identical to or different from this, $R^{18}$ denotes hydroxyl, benzyloxy or a radical of the formula $-NH-CO-NH_2$,

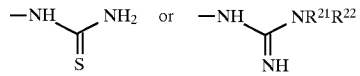

wherein $R^{21}$ and $R^{22}$ are identical or different and denote hydrogen or straight-chain or branched alkyl having up to 4 carbon atoms, which can in turn be substituted by phenyl or pyridyl, $R^{20}$ denotes hydrogen or a sodium ion, and/or in turn are optionally substituted up to twice in an identical or different manner by carboxyl, halogen, cyano, mercapto, formyl, trifluoromethyl, nitro, phenyl, straight-chain or branched alkoxy, alkoxycarbonyl, alkylthio or acyl having in each case up to 6 carbon atoms or by straight-chain or branched alkyl having up to 6 carbon atoms, which can in turn be substituted by hydroxyl, azido, by straight-chain or branched alkoxy or acyl having up to 5 carbon atoms or by a group of the formula $-NR^{23}R^{24}$, $R^{25}-S-$, $R^{26}-SO_2O-$ or

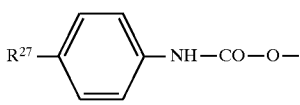

wherein
$R^{23}$ and $R^{24}$ have the abovementioned meaning of $R^7$ and $R^8$ and are identical to or different from these, or denote a radical of the formula —P(O) (OR$^{28}$) (OR$^{29}$) or $R^{30}$—SO$_2$—
wherein
$R^{28}$ and $R^{29}$ are identical or different and denote hydrogen or straight-chain or branched alkyl having up to 3 carbon atoms and
$R^{30}$ denotes methyl, phenyl or tolyl,
$R^{25}$ denotes a radical of the formula

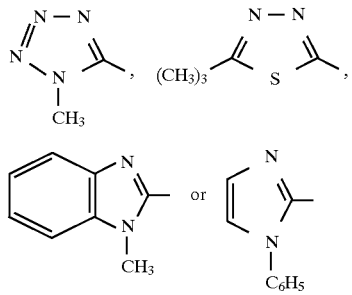

$R^{26}$ denotes straight-chain or branched alkyl having up to 3 carbon atoms,
$R^{27}$ denotes straight-chain or branched alkoxycarbonyl having up to 6 carbon atoms or carboxyl
and/or
the cyclic radicals are optionally substituted by a radical of the formula

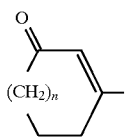

wherein
n denotes a number 0, 1 or 2,
and salts and N-oxides thereof.

The compounds according to the invention can exist in stereoisomeric forms which either behave as mirror images (enantiomers) or do not behave as mirror images (diastereomers). The invention relates both to the enantiomers or diastereomers . . . separated in a known manner into the stereoisomerically uniform constituents.

Physiologically acceptable salts of the 6-membered heteroaryl-oxazolidinones can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts with customary bases may be mentioned as the salts, such as, for example, alkali metal salts (for example sodium or potassium salts), alkaline earth metal salts (for example calcium or magnesium salts) or ammonium salts derived from ammonia or organic amines, such as, for example, diethylamine, triethylamine, ethyldiisopropylamine, procaine, dibenzylamine, N-methylmorpholine, dihydroabiethylamine, 1-ephenamine or methyl-piperidine.

$C_1$–$C_4$-alkyl halides, in particular $C_1$–$C_4$-alkyl iodides, can furthermore function as salts.

In the context of the invention, a heterocyclic radical under substituent D in the case of direct bonding to the oxazolidino skeleton in general represents a 6-membered, aromatic heterocyclic radical which has at least one nitrogen atom and is bonded directly via a carbon atom, or represents a bi- or tricyclic aromatic radical which has at least one nitrogen-containing ring, is bonded directly via a carbon atom and is in each case 6-membered, or represents β-carbolin-3-yl, or represents indolizinyl bonded directly via the 6-membered ring. Examples which may be mentioned are cinnolinyl, pteridinyl, phenanthridinyl, acridinyl, phenanthrolinyl, quinazolinyl, quinoxalinyl, naphthyridinyl, phthalazinyl, quinolyl, isoquinolyl, 4H-quinolizinyl, phenazinyl, pyridyl, pyrazinyl, pyrimidinyl, pyridazinyl, indolizinyl, β-carbolin-3-yl, and indolizinyl bonded directly via the 6membered ring.

In the further field of substitution, a heterocylic radical also represents a 5- to 6-membered, saturated or unsaturated ring which can contain up to 3 oxygen, sulphur and/or nitrogen atoms as heteroatoms. Preferred rings which are mentioned are: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl or piperazinyl.

These also include 5- to 6-membered saturated heterocyclic rings which are bonded via N and can contain up to 2 oxygen, sulphur and/or nitrogen atoms as hetero atoms, such as, for example, piperidyl, morpholinyl or piperazinyl or pyrrolidinyl. Piperidyl and pyrrolidinyl are particularly, preferred.

Hydroxyl-protective group in the context of the abovementioned definition in general represents a protective group from the series consisting of: trimethylsilyl, triisopropylsilyl, tert-butyldimethylsilyl, benzyl, benzyloxycarbonyl, 2-nitrobenzyl, 4nitrobenzyl, tert. butyloxycarbonyl, allyloxycarbonyl, 4-methoxybenzyl, 4-methoxybenzyloxcarbonyl, tetrahydropyranyl, formyl, acetyl, trichloroacetyl, 2,2,2-trichloroethoxycarbonyl, methoxyethoxymethyl, [2-(trimethylsilyl)-ethoxy]methyl, benzoyl, 4-methoxybenzoyl, 4-nitrobenzoyl, 4-fluorobenzoyl, 4-chlorobenzoyl or 4-methoxybenzoyl. Acetyl, tert-butyldimethylsilyl and tetahydropyranyl are preferred.

Amino-protective group in the context of the invention are the customary amino-protective groups used in peptide chemistry.

These include, preferably: benzyloxcarbonyl, 2,4-dimethoxybenzyloxycarbonyl, 4-methoxybenzyloxycarbonyl, methoxycarbonyl, ethoxycarbonyl, tert-butoxycarbonyl, allyloxycarbonyl, phthaloyl, 2,2,2-trichloroethoxycarbonyl, fluorenyl-9-methoxycarbonyl, formyl, acetyl, 2-chloroacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dintrobenzyl, 4-nitrophenyl, 4-methoxyphenyl or triphenylmethyl.

Preferred compounds are those of the general formula () in which
$R^1$ represents azido or hydroxyl, or represents a group of the formula —OR$^2$, —OSO$_2$R$^3$ or —NR$^4$R$^5$,
wherein R² denotes straight-chain or branched acyl having up to 6 carbon atoms or benzyl, R³ denotes straight-chain or branched alkyl having up to 3 carbon atoms, phenyl or tolyl, R⁴ and R⁵ are identical or different and denote cyclopropyl, cyclopentyl, cyclohexyl, hydrogen, phenyl or straight-chain or branched alkyl having up to 6 carbon atoms, tert-butoxycarbonyl or benzyloxcarbonyl, or R⁴ or R⁵ denotes a group of the formula —CO—R⁶, wherein denotes cyclopropyl, cyclobutyl, cyclopentyl, cyclohexyl or straight-chain or branched alkyl having up to 6 carbon atoms, phenyl or hydrogen, D represents cinnolinyl, pteridinyl, acridinyl, quinazolinyl, quinoxalinyl, naphthyridinyl, phthalazinyl, quinolyl, isoquinolyl, pyridyl, pyrazinyl, pyrimidinyl or pyridazinyl, wherein the cyclic radicals are optionally substituted in each case up to 3 times in an identical or different manner by carboxyl, fluorine, chlorine, bromine, iodine, cyano, mercapto, trifluoromethyl, formyl, nitro, straight-chain or branched alkoxy, alkoxycarbonyl, alkylthio or acyl having in each case up to 4 carbon atoms or by straight-chain or branched alkyl having up to 4 carbon atoms, which can in turn optionally be substituted by hydroxyl, by straight-chain or branched alkoxy or acyl having up to 4 carbon atoms or by a group of the formula —NR⁷R⁸, wherein R⁷ and R⁸ are identical or different and denote hydrogen, formyl, straight-chain or branched alkyl or acyl having in each case up to 3 carbon atoms, phenyl, cyclopropyl, cyclopentyl or cyclohexyl, or together with the nitrogen atom form a morpholinyl, pyrrolidinyl, piperazinyl or piperidyl ring which are optionally substituted, including via the free N function, by phenyl, pyrimidyl, methyl, ethyl or acetyl, and/or the cyclic radicals are optionally substituted by a group of the formula —NR⁷R⁸', wherein R⁷ and R⁸' have the abovementioned meaning of R⁷ and R⁸ and are identical to or different from these, and/or the cyclic radicals are optionally substituted by (C₂–C₄)-alkenylphenyl, phenyl, pyridyl or thienyl, which in turn are optionally substituted by a group of the formula —CO—NR⁹R¹⁰, —NR¹¹R¹², —NR¹³—SO₂—R¹⁴, R¹⁵R¹⁶N—SO₂—, R¹⁷—S(O)ₐ—, R¹⁸—N=CH— or by the radical —CH(OH)—SO₃R²⁰, wherein a denotes a number 0, 1 or 2, R⁹, R¹⁰, R¹³, R¹⁵ and R¹⁶ are identical or different and denote hydrogen, straight-chain or branched alkyl having up to 4 carbon atoms, tolyl or phenyl, R¹¹ and R¹² are identical or different and have the abovementioned meaning of R⁷ and R⁸ and are identical to or different from these, R¹⁴ and R¹⁷ are identical or different and have the abovementioned meaning of R³ and are identical to or different from this, R¹⁸ denotes hydroxyl, benzyloxy or a radical of the formula

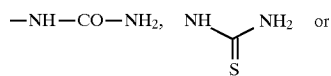

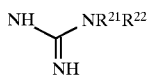

wherein

R²¹ and R²² are identical or different and denote hydrogen or straight-chain or branched alkyl having up to 3 carbon atoms, which can in turn be substituted by phenyl or pyridyl, R²⁰ denotes hydrogen or a sodium ion and/or in turn are optionally substituted up to twice in an identical or different manner by carboxyl, fluorine, chlorine, bromine, iodine, cyano, mercapto, trifluoromethyl, formyl, nitro, phenyl, straight-chain or branched alkoxy, alkoxycarbonyl, alkylthio or acyl having in each case up to 4 carbon atoms or by straight-chain or branched alkyl having up to 4 carbon atoms, which can in turn be substituted by hydroxyl, azido, by straight-chain or branched alkoxy or acyl having up to 4 carbon atoms or by a group of the formula —NR²³R²⁴, R²⁵—S—, R²⁶—SO₂O— or

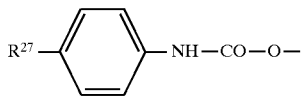

wherein

R²³ and R²⁴ have the abovementioned meaning of R⁷ and R⁸ and are identical or different from these, or a radical of the formula (P)(O)(OR²⁸)(OR²⁹) or R³⁰—SO₂—, wherein R²⁸ and R²⁹ are identical or different and denote hydrogen, methyl or ethyl, R³⁰ denotes methyl, phenyl or tolyl, R²⁵ denotes a radical of the formula

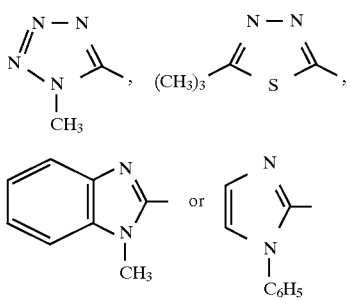

R²⁶ denotes methyl, ethyl, propyl or isopropyl,

R²⁷ denotes straight-chain or branched alkoxycarbonyl having up to 5 carbon atoms or carboxyl and/or the cyclic radicals are optionally substituted by a radical of the formula

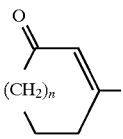

wherein
n denotes a number 0, 1 or 2,
and salts and N-oxides thereof.

Particularly preferred compounds are those of the general formula (I),
in which
$R^1$ represents azido or hydroxyl, or represents a group of the formula $-OR^2$, $-OSO_2R^3$ or $-NR^4R^5$,
wherein
$R^2$ denotes straight-chain or branched acyl having up to 6 carbon atoms,
$R^3$ denotes methyl, ethyl, phenyl or tolyl,
$R^4$ and $R^5$ are identical or different and denote cyclopropyl, cyclopentyl, cyclohexyl, hydrogen, phenyl or straight-chain or branched alkyl having up to 5 carbon atoms,
or
$R^4$ or $R^8$ denotes agroup of the formula $-CO-R^6$,
wherein
$R^6$ denotes cyclopropyl, cyclopentyl, cyclohexyl or straight-chain or branched alkyl having up to 4 carbon atoms, hydrogen or phenyl,
D represents cinnolinyl, quinoxalinyl, naphthyridinyl, phthalazinyl, quinolyl, isoquinolyl, pyridyl, pyrazinyl, pyrimidinyl or pyridazinyl, wherein the cyclic radicals are optionally substituted in each case up to twice in an identical or different manner by carboxyl, fluorine, chlorine, bromine, iodine, cyano, formyl, trifluoromethyl, nitro, straight-chain or branched alkoxy, alkoxycarbonyl or acyl having in each case up to 4 carbon atoms or by straight-chain or branched alkyl having up to 4 carbon atoms, which can in turn be optionally substituted by hydroxyl, by straight-chain or branched alkoxy or acyl having up to 4 carbon atoms or by a group of the formula $-NR^7R^8$,
wherein
$R^7$ and $R^8$ are identical or different and denote hydrogen, formyl, acetyl, methyl or cyclopropyl, or together with the nitrogen atom form a morpholinyl, pyrrolidinyl, piperazinyl or piperidyl ring, which are optionally substituted, including via the free N function, by methyl, ethyl, phenyl, pyrimidyl or acetyl,
and/or the cyclic radicals are optionally substituted by a group of the formula $-NR^{7'}R^{8'}$,
wherein
$R^{7'}$ and $R^{8'}$ have the abovementioned meaning of $R^7$ and $R^8$ and are identical to or different from these,
and/or
the cyclic radicals are optionally substituted by 2-phenylvinyl, phenyl, pyridyl or thienyl, which are in turn optionally substituted by a group of the formula $-CO-NR^9R^{10}$, $-NR^{11}R^{12}$, $R^{18}-N=CH-$ or by the radical $-CH(OH)-SO_3-R^{20}$,
wherein
$R^9$ and $R^{10}$ are identical or different and denote hydrogen or methyl,
$R^{11}$ and $R^{12}$ are identical or different and have the abovementioned meaning of $R^7$ and $R^8$ and are identical to or different from these, $R^{18}$ denotes hydroxyl, benzyloxy or a radical of the formula $-NH-CO-NH_2$,

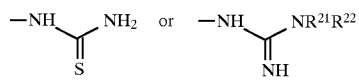

wherein
$R^{21}$ and $R^{22}$ are identical or different and denote hydrogen, methyl or ethyl, which can in turn be substituted by phenyl or pyridyl,
$R^{20}$ denotes hydrogen or a sodium ion,
and/or are in turn optionally substituted up to twice in an identical or different manner by carboxyl, fluorine, chlorine, bromine, iodine, cyano, formyl, trifluoromethyl, nitro, phenyl, straight-chain or branched alkoxy, alkoxycarbonyl or acyl having in each case up to 4 carbon atoms or by straight-chain or branched alkyl having up to 4 carbon atoms, which can in turn be substituted by hydroxyl, azido, by straight-chain or branched alkoxy or acyl having up to 4 carbon atoms or by a group of the formula $-NR^{23}R^{24}$, $R^{25}-S-$, $R^{26}-SO_2O-$ or,

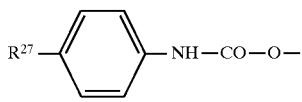

wherein
$R^{23}$ and $R^{24}$ have the abovementioned meaning of $R^7$ and $R^8$ and are identical to or different from these, or denote a radical of the formula $P(O)(OCH_3)_2$ or $R^{30}-SO_2-$
wherein
$R^{30}$ denotes methyl, phenyl or tolyl,
$R^{25}$ denotes a radical of the formula

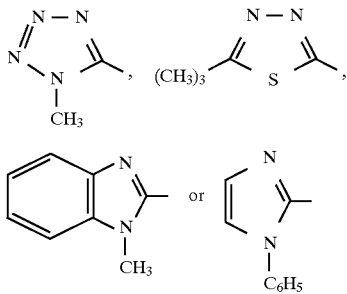

$R^{26}$ denotes methyl, ethyl or propyl,
$R^{27}$ denotes straight-chain or branched alkoxycarbonyl having up to 4 carbon atoms
and/or
the cyclic radicals are optionally substituted by a radical of the formula

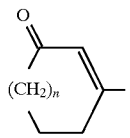

wherein
n denotes a number 0, 1 or 2,
and salts and N-oxides thereof.

Processes have furthermore been found for the preparation of the compounds of the general formula (I) according to the invention, characterized in that

[A] compounds of the general formulae (II) or (III)

$$D\text{—}N\text{=}C\text{=}O \quad (II)$$

or

$$D\text{—}CO\text{—}N_3 \quad (III)$$

in which
D has the abovementioned meanings,
are reacted with lithium bromide/$(C_4H_9)_3$ P(O) and epoxides of the general formula (IV)

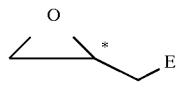

(IV)

in which
E represents $C_1$–$C_6$-acyloxy,
in inert solvents, if appropriate in the presence of a base, and in the case where $R^1$=OH, the hydroxyl function is liberated by a typical ester hydrolysis or by a typical transesterification,
or

[B] compounds of the general formula (V)

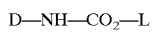

$$D\text{—}NH\text{—}CO_2\text{—}L \quad (V)$$

in which
D has the abovementioned meaning
and
L represents a typical protective group, preferably benzyl, are reacted in inert solvents and in the presence of a base, for example lithium alkyls or lithium N-alkyl- or lithium N-silylalkylamides, preferably n-butyllithium, with epoxides of the general formula (IV),
or

[C] in the case where $R^1$=OH, compounds of the general formula (III) are first converted, by splitting off nitrogen in alcohols, into the compounds of the general formula (Va)

$$D\text{—}NH\text{—}CO_2\text{—}T \quad (Va)$$

in which
D has the abovementioned meaning
and
I represents straight-chain or branched $C_2$–$C_6$-alkyl preferably n-butyl,
and in a second step these compounds are reacted as described under [A] in inert solvents and in the presence of a base, preferably lithium N-alkyl- or N-silylalkylamides or n-butyllithium and epoxides of the general formula (IV),
or

[D] the compounds of the general formula (VI)

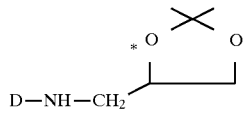

(VI)

in which
D has the abovementioned meaning,
either are reacted directly with acids and diethyl carbonate, or the compounds of the general formula (VII)

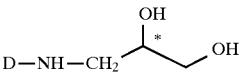

(VII)

in which
D has the abovementioned meaning,
are first prepared by reaction of the compounds of the general formula (VI) with acids of the general formula (VII), and are then cyclized in the presence of an auxiliary, in inert solvents,
or

[E] compounds of the general formula (Ia)

(Ia)

in which
D has the abovementioned meaning,
are first converted, by reaction with ($C_1$–$C_4$)alkyl or phenylsulphonyl chlorides in inert solvents and in the presence of a base, into the corresponding compounds of the general formula (Ib)

(Ib)

in which
D and $R^3$ have the abovementioned meaning,
and the azides of the general formula (Ic)

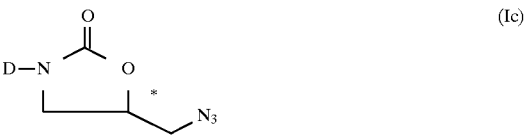

(Ic)

in which
D has the abovementioned meaning,
are then prepared with sodium azide in inert solvents,
in a further step these are converted, by reaction with $(C_1\text{–}C_4\text{—}O)_3\text{—}P$ or $PPh_3$, preferably $(CH_3O)_3P$, in inert solvents and with acids, into the amines of the general formula (Id)

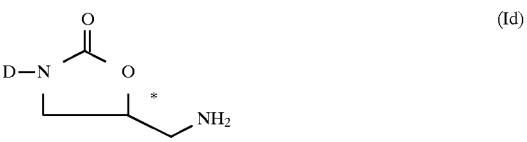

(Id)

in which
D has the abovementioned meaning,
and by reaction with acetic anhydride or other acylating agents of the general formula (VIII)

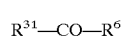

$$R^{31}\text{—}CO\text{—}R^6 \quad (VII)$$

in which
$R^6$ has the abovementioned meaning
and
$R^{31}$ represents halogen, preferably chlorine or represents the radical —$OCOR^6$.

in inert solvents, the compounds of the general formfula (Ie)

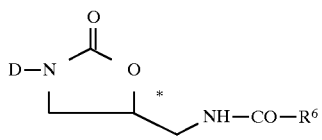
(Ie)

in which
D and $R^6$ have the abovementioned meaning,
are prepared,
or
[F] compounds of the general formula (Ie) are converted, by halogenation, if appropriate in the presence of a silver catalyst, into the compounds of the general formula (If)

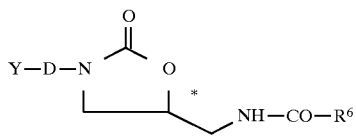
(If)

in which
Y represents halogen, preferably bromine or iodine
and
D and $R^6$ have the abovementioned meaning,
or
[G] compounds of the general formula (If) are reacted with compounds of the general formula (IX)

$$D'\text{—}R^{32} \quad (IX)$$

in which
D' represents one of the optionally substituted monocyclic heterocyclic radicals listed above under D, phenyl or $(C_2\text{–}C_8)$-alkenylphenyl
and
$R^{32}$ represents the boronic acid radical —$B(OH)_2$, or represents an organotin radical of the formula —$SnR^{33}R^{34}R^{35}$,
wherein
$R^{33}$, $R^{34}$ and $R^{35}$ are identical or different and denote $C_1\text{–}C_4$-alkyl,
in inert solvents and in the presence of a palladium catalyst,
and in the case of the N-oxides, an oxidation is carried out,
and in the case where $R^4$, $R^5$, $R^9$, $R^{10}$, $R^{11}$, $R^{12}$, $R^{13}$, $R^{15}$, $R^{16}$, $R^{18}$ and $R^{19} \neq H$, an alkylation is carried out by customary methods,
and if appropriate further substituents or functional groups which are already present are introduced or, respectively, derivatized by customary methods, such as, for example, redox reactions, substitution reactions and/or hydrolysis or incorporation and breakdown of protective groups.

The processes according to the invention can be illustrated by way of example by the following equations:

[A]

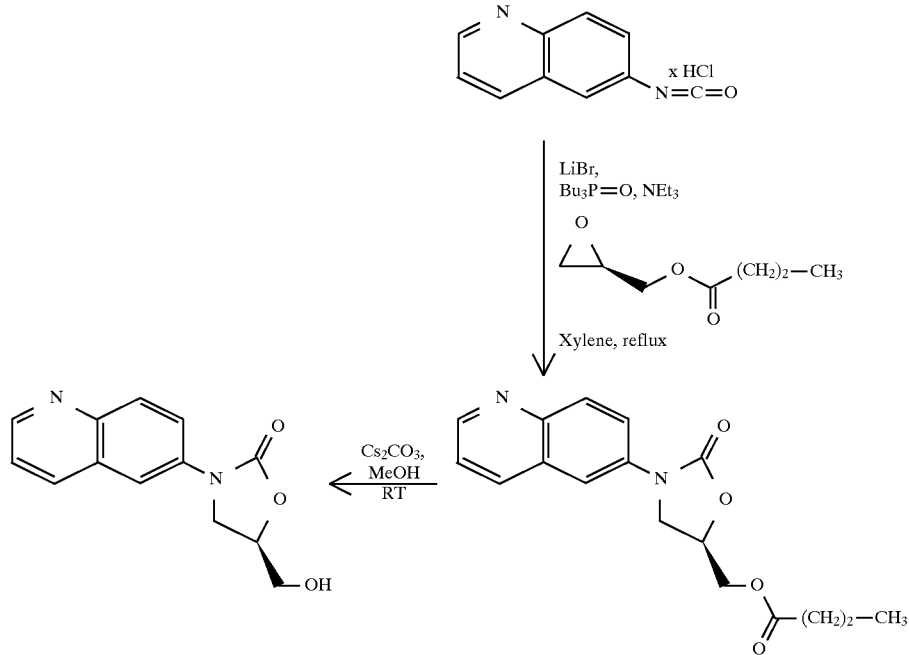

-continued
[A]
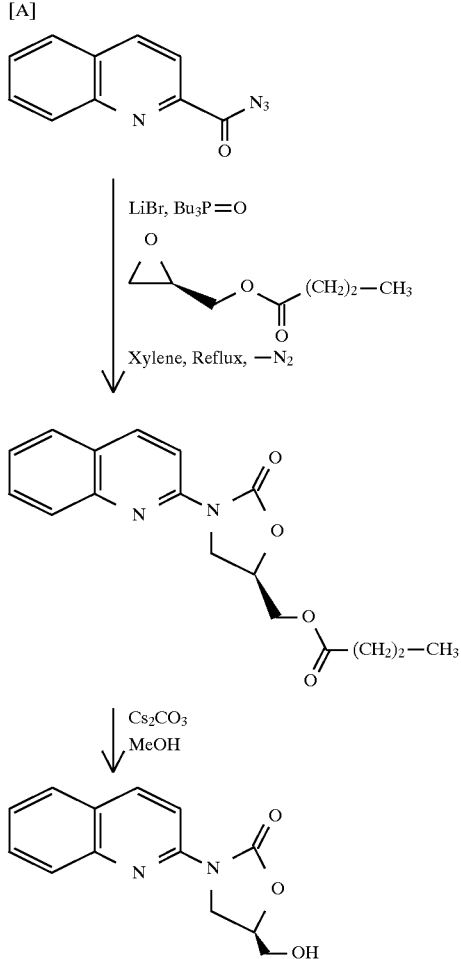
[B]
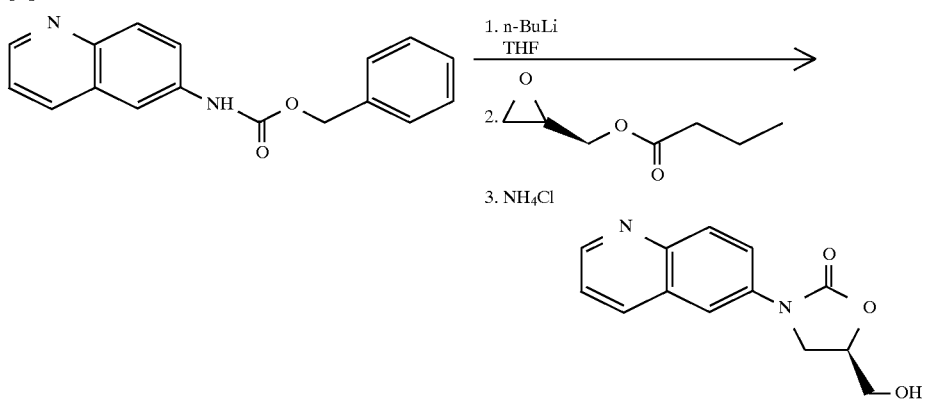
[C]

-continued
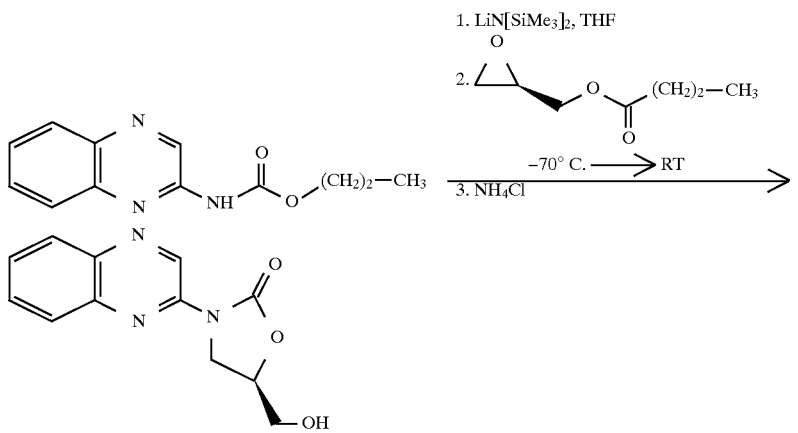
[D]
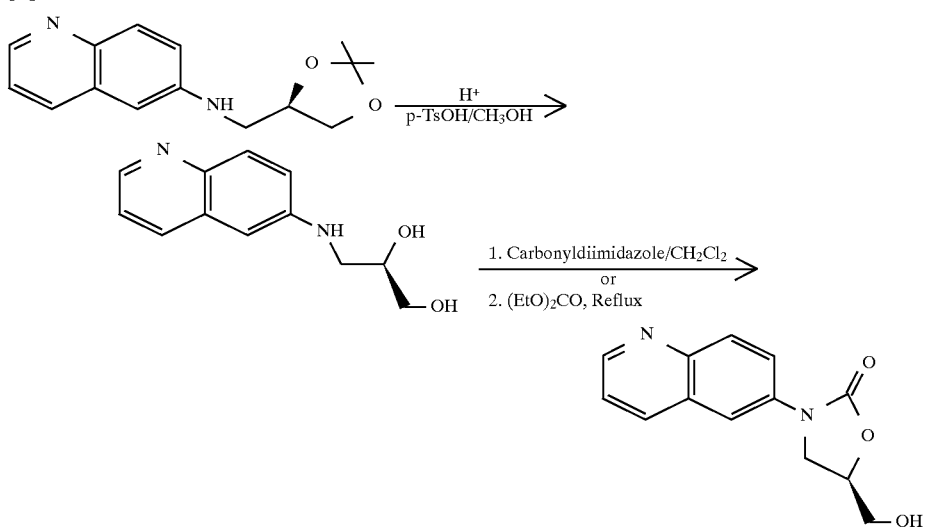
[E]
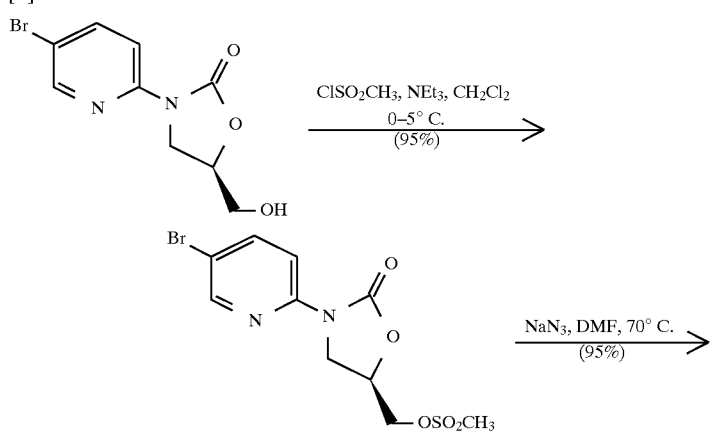
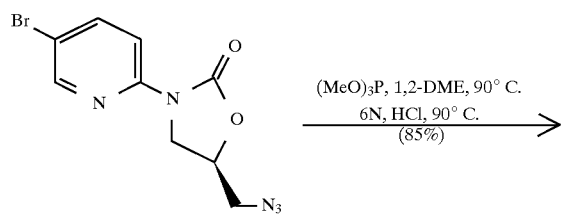

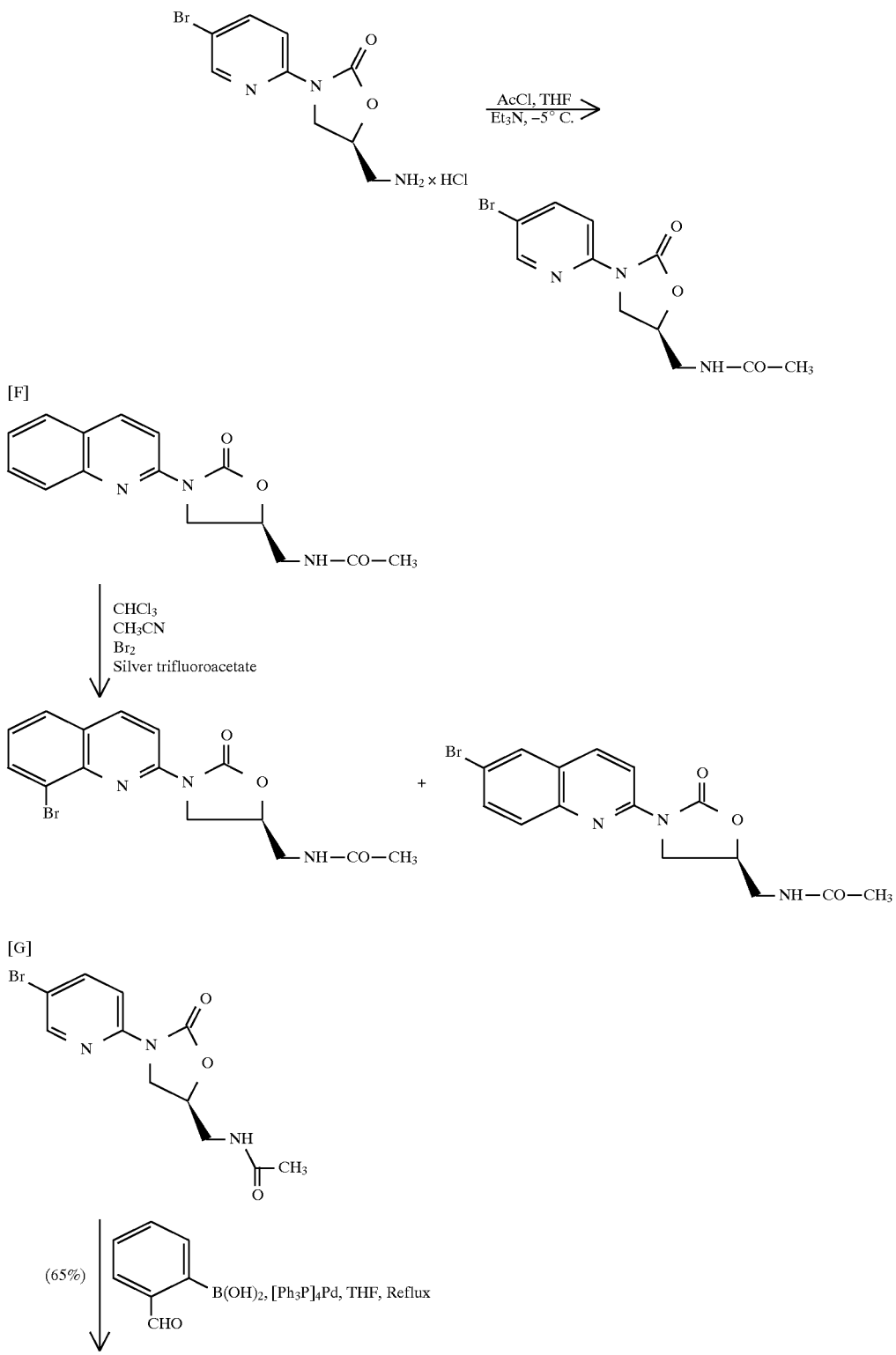

-continued

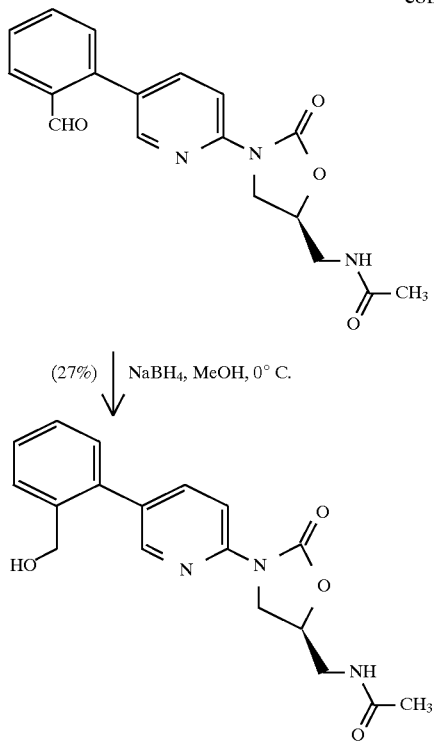

(27%) | NaBH₄, MeOH, 0° C.

Suitable solvents are, according to the individual process steps, the customary solvents which do not change under the reaction conditions. These include, preferably, alcohols, such as methanol, ethanol, propanol or isopropanol, or ethers, such as diethyl ether, dioxane, 1,2-dimethoxyethane, tetrahydrofuran, glycol dimethyl ether, tert-butyl methyl ether, or ketones, such as acetone or butanone, amides, such as dimethylformamide or hexamethyl-phosphoric acid triamide, or hydrocarbons, such as hexane, benzene, dichlorobenzene, xylene or toluene, or dimethyl sulphoxide, acetonitrile, ethyl acetate or halogenated hydrocarbons, such as methylene chloride, chloroform or carbon tetrachloride, or pyridine, picoline or N-methylpiperidine. Mixtures of the solvents mentioned can also be used.

Suitable bases are, according to the individual process steps, the customary inorganic or organic bases. These include, preferably, alkali metal hydroxides, such as, for example, sodium hydroxide or potassium hydroxide, or alkali metal carbonates, such as sodium carbonate or potassium carbonate, or alkali metal alcoholates, such as, for example, sodium methanolate or potassium methanolate or sodium ethanolate or potassium ethanolate, or organic amines, such as ethyldiisopropylamine, triethylamine, picoline, pyridine or N-methylpiperidine, or amides, such as sodium amide or lithium diisopropylamide, or lithium N-silylalkylamides, such as, for example, lithium N-(bis) triphenylsilylamide, or lithium alkyls, such as n-butyllithium.

The base is employed in an amount of 1 mol to 10 mol, preferably 1 mol to 3 mol, per mol of the compounds of the general formulae (II), (III) and (IV) and (Va).

All the reactions are in general carried out under normal, increased or reduced pressure (for example 0.5 to 5 bar). The reactions are in general carried out under normal pressure.

Process [A] is preferably carried out in xylene or dichlorobenzene, if appropriate in the presence of triethylamine, under reflux.

The base-catalysed transesterification is carried out with one of the abovementioned alcohols, preferably methanol, in a temperature range from −10° C. to +40° C., preferably at room temperature.

Suitable bases are in general sodium bicarbonate, sodium methanolate, hydrazine hydrate, potassium carbonate or caesium carbonate. Caesium carbonate is preferred.

Process [B] is carried out in one of the abovementioned ethers with lithium alkyl compounds or lithium N-silylamides, such as, for example, n-butyllithium, lithium diisopropylamide or lithium bis-trimethylsilylamide, preferably in tetrahydrofuran and lithium bis-trimethylsilylamide or n-butyllithium, in a temperature range from −100° C. to +20° C., preferably from −75° C. to −40° C.

For process [C], the abovementioned alcohols are preferably suitable for the first step, and tetrahydrofuran is suitable in the case of the subsequent cyclization.

Suitable bases for the cyclization are preferably the abovementioned lithium N-alkylsilyl compounds or n-butyllithium, n-Butyllithium is particularly preferred.

The first reaction step is carried out at the boiling point of the corresponding alcohol, and the cyclization is carried out in a temperature range from −70° C. to room temperature.

The cyclization [D] is carried out in the presence of an auxiliary and/or presence of an acid.

Suitable acids are in general inorganic acids, such as, for example, hydrochloric acid and sulphuric acid, or organic carboxylic acids having 1–6 C atoms, which are optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals, such as, for example, methanesulphonic acid, ethanesulphonic acid, benzenesulphonic acid or toluenesulphonic acid. Hydrochloric acid is particularly preferred.

The acid is employed in an amount of 1 mol to 10 mol, preferably 1 mol to 2 mol, per mol of the compounds of the general formula (VI).

Suitable auxiliaries are the customary reagents, such as phosgene, carbonyldiimidazole or diethyl carbonate or trichloromethyl chloroformate. Carbonyldiimidazole, diethyl carbonate or trichloromethyl chloroformate are preferred.

Suitable solvents are the abovementioned halogenated hydrocarbons. Methylene chloride is preferred.

The cyclizations are in general carried out in a temperature range from −20° C. to 100° C., preferably at −20° C. to room temperature.

The acylation [E] is in general carried out in one of the abovementioned ethers or halogenated hydrocarbons, preferably tetrahydrofuran or methylene chloride, in a temperature range from −30° C. to 50° C., preferably from −10° C. to room temperature.

The coupling reactions [G] with the boronic acid compounds and tin aryl compounds are likewise carried out in one of the abovementioned ethers or hydrocarbons, preferably tetrahydrofuran or toluene, and in the presence of a palladium complex.

Suitable palladium complexes are, for example, Pd[P(C$_6$H$_5$)$_3$]$_4$, [(C$_6$H$_5$)$_3$P]$_2$PdCl$_2$ or (C$_6$H$_5$CN)$_2$PdCl$_2$. [(C$_6$H$_5$)$_3$P]$_4$Pd is preferred.

The reaction is carried out in a temperature range from room temperature to 150° C., preferably at the boiling point of the particular solvent.

The reductions are in general carried out with hydrides in inert solvents with boranes, diboranes or their complex compounds.

The reductions are preferably carried out with hydrides, such as complex borohydrides or aluminium hydrides, as well as boranes. Sodium borohydride, lithium borohydride, sodium cyanoborohydride, lithium aluminium hydride, sodium bis-(2-methoxyethoxy)aluminium hydride or borane tetrahydrofuran are particularly preferably employed here.

The reduction is in general carried out in a temperature range from −50° C. up to the particular boiling point of the solvent, preferably from −20° C. to +90° C.

The reductions can in general be carried out by hydrogen in water or in inert organic solvents, such as alcohols, ethers or halogenated hydrocarbons, or mixtures thereof with catalysts, such as Raney nickel, palladium, palladium-on-animal charcoal or platinum, or with hydrides or boranes in inert solvents, if appropriate in the presence of a catalyst.

The reaction is preferably carried out with hydrides, such as complex borohydrides or aluminium hydrides. Sodium borohydride, lithium aluminium hydride or sodium cyanoborohydride are particularly preferably employed here.

Suitable solvents here are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, or amides, such as hexamethylphosphoric acid triamide or dimethylformamide, or acetic acid. It is also possible to use mixtures of the solvents mentioned.

The oxidation to give the N-oxide is in general carried out in one of the abovementioned solvents, preferably in methylene chloride, with oxidizing agents, such as, for example, metachloroperbenzoic acid, hydrogen peroxide or peracetic acid, preferably with metachloroperbenzoic acid, in a temperature range from 0° C. to 80° C., preferably from 0° C. to 40° C.

The hydroxyl-protective groups are in general split off by a customary method, for example by hydrogenolytic cleavage of the benzyl ethers in the abovementioned inert solvents in the presence of a catalyst using hydrogen gas.

The amino-protective group is in general likewise split off by customary methods, and in particular, preferably, Boc is split off with hydrochloric acid in dioxane, Fmoc is split off with piperidine and Z is split off with HBr/HOAc or by hydrogenolysis.

The other derivatization reactions mentioned above are in general carried out by the methods published in Compendium of Organic Synthetic Methods. T. T. Harrison and S. Harrison, Wiley Interscience.

Redox reactions, reductive amination, transesterification and halogenation of methyl groups with N-bromosuccinimide (NBS) or N-chlorosuccinimide (NCS) are mentioned as preferred and are explained by way of example below.

Suitable solvents for the alkylation are the customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, or triethylamine, pyridine, dimethyl sulphoxide, dimethylformamide, acetonitrile, acetone or nitromethane. It is also possible to use mixtures of the solvents mentioned. Methylene chloride, dimethyl sulphoxide and dimethylformamide are preferred.

The alkylation is carried out in the abovementioned solvent at temperatures of 0° C. to +150° C., preferably at room temperatures up to +100° C., under normal pressure.

The amidation and the sulphoamidation are in general carried out in inert solvents in the presence of a base and a dehydrating agent.

Suitable solvents here are inert organic solvents which do not change under the reaction conditions. These include halogenated hydrocarbons, such as methylene chloride, chloroform, carbon tetrachloride, 1,2-dichloroethane, trichloroethane, tetrachloroethane, 1,2-dichloroethane or trichloroethylene, hydrocarbons, such as benzene, xylene, toluene, hexane, cyclohexane or petroleum factions, nitromethane, dimethylformamide, acetonitrile or tetrahydrofuran. It is also possible to employ mixtures of the solvents. Methylene chloride and tetrahydrofuran are particularly preferred.

Suitable bases for the amidation and the sulphoamidation are the customary basic compounds. These include, preferably, alkali metal and alkaline earth metal hydroxides, such as lithium hydroxide, sodium hydroxide, potassium hydroxide or barium hydroxide, alkali metal hydrides, such as sodium hydride, alkali metal carbonates or alkaline earth metal carbonates, such as sodium carbonate or potassium carbonate, or alkali metal alcoholates, such as, for example, sodium methanolate or ethanolate, potassium methanolate or ethanolate or potassium tert-butylate, or organic amines, such as benzyltrimethylammonium hydroxide, tetrabutylammonium hydroxide, pyridine, triethylamine or N-methylpiperidine.

The amidation and the sulphoamidation are in general carried out in a temperature range from 0° C. to 150° C., preferably at 25° C. to 40° C.

The amidation and the sulphoamidation are in general carried out under normal pressure. However, it is also possible to carry out the process under reduced pressure or under increased pressure (for example in a range from 0.5 to 5 bar).

In carrying out the amidation and the sulphoamidation, the base is in general employed in an amount of 1 to 3 mol, preferably 1 to 1.5 mol, per mol of the particular carboxylic acid.

Suitable dehydrating reagents are carbodiimides, such as, for example, diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl 1,2-oxazolium-3-sulphonate, or propanephosphoric acid anhydride or isobutyl chloroformate or benzotriazolyloxy-tris-(dimethylamino) phosphonium hexafluorophosphate or phosphonic acid diphenyl ester-amide or methanesulphonyl chloride, if appropriate in the presence of bases, such as triethylamine or N-ethylmorpholine or N-methylpiperidine or 4-dimethylaminopyridine.

Suitable bases for the hydrolysis are the customary inorganic bases. These include, preferably, alkali metal hydroxides or alkaline earth metal hydroxides such as for example sodium hydroxide, potassium hydroxide or barium hydroxide, or alkali metal carbonates, such as sodium carbonate or potassium carbonate or sodium bicarbonate. Sodium hydroxide or potassium hydroxide are particularly preferably employed.

Suitable solvents for the hydrolysis are water or the organic solvents customary for a hydrolysis. These include, preferably, alcohols, such as methanol, ethanol, propanol, isopropanol, butanol or ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably 1 to 1.5 mol, per mol of the ester. Molar amounts of the reactants are particularly preferably used.

The esterification is in general carried out with the corresponding alcohols in the presence of acids, preferably sulphuric acid, in a temperature range from 0° C. to 150° C., preferably from 50° C. to 100° C., under normal pressure.

The compounds of the general formulae (IV), (VIII) and (IX) are known or can be prepared by customary methods.

The compounds of the general formula (VII) are new in most cases and can be prepared, for example, as described above.

The compounds of the general formula (II) are known in some cases or are new, and can then be prepared, for example, by reacting the corresponding amines with trichloroethyl chloroformate in one of the abovementioned solvents, preferably xylene, at the reflux temperature.

The compounds of the general formula (III) are known in some cases or are new, and can then be prepared, for example, starting from the corresponding carboxylic acids, by reaction either with isobutyl, chloroformate/acetone, sodium azide/water or with diphenylphosphoryl azide/ tetrahydrofuran or with xylene or methylene chloride in the presence of one of the abovementioned bases, preferably triethylamine, at −10° C. to room temperature.

The compounds of the general formulae (V) and (Va) are known in some cases or are new, and can be prepared either by splitting off nitrogen from the corresponding carboxylic acid azides and reaction with the corresponding alcohols, or by reaction of the corresponding amines with chloroformic esters, preferably benzyl chloroformate, in one of the abovementioned solvents, preferably tetrahydrofuran or dioxane, in a temperature range from −10° C. to 200° C., preferably from 0° C. to 150° C.

The compounds of the general formula (VII) are new in most cases and can be prepared as described above.

The compounds of the general formula (a) are new and can be prepared, for example, as described under [A], [B], [D] or [E].

The compounds of the general formula (Ib), (Ic), (Id), (Ie) and (If) are new and can be prepared as described above.

The compounds of the general formula (VI) are known in most cases or are new and can be prepared, for example, starting from the free amines (Ia) by reaction either with the acetonide of glycerolaldehyde in methanol and in the presence of sodium acetate/sodium cyanoborohydride or of sodium boranate and methanol in a temperature range from −20° C. to +40° C., preferably from −10° C. to 20° C., under normal pressure.

The halogen atom Y (compounds of the general formula (If)) is introduced in the case of bromine and iodine either with elemental bromine or iodine or in the presence of a silver salt in one of the abovementioned solvents, preferably methylene chloride, acetonitrile or chloroform, in a temperature range from −30° C. to +60° C. preferably from 0° C. to +30° C., under normal pressure.

Suitable silver salts are, for example, silver tetrafluoroborate, silver trifluoromethanesulphonate or silver trifluoroacetate.

The minimum inhibitory concentrations (MIC) were determined by the series dilution method on Iso-Sensitest agar (Oxoid). A series of agar plates which contained concentrations of the active compound which decreased by two-fold dilution in each case were prepared for each test substance. The agar plates were inoculated with a Multipoint inoculator (Denley). Overnight cultures of the pathogens which had been diluted beforehand such that each inoculation point contained about $10^4$ colony-forming particles were used for the inoculation. The inoculated agar plates were incubated at 37° C. and the germ growth was read off after about 20 hours. The MIC value ($\mu$g/ml) indicates the lowest concentration of active compound at which no growth was detectable with the naked eye.

The MIC values were determined with the aid of the microdilution method in BH medium. Each test substance was dissolved in the nutrient medium. A concentration series of the test substances was prepared in the microtiter plate by serial dilution. Overnight cultures of the pathogens which were diluted 1:250 beforehand in the nutrient medium were used for the inoculation. In each case 100 $\mu$l of inoculation solution were added to 100 $\mu$l of the diluted nutrient solutions containing the active compound.

The microtiter plates were incubated at 37° C. and read off after about 20 hours. The MIC value ($\mu$g/ml) indicates the lowest concentration of active compound at which no growth was detectable.

MIC values (µ/ml):

| Ex. No. | Staph. 133 | Staph. 48N | Staph 25701 | Staph. 9TV | E. coli Neumann | Klebs. 57 USA | Psdm. Bonn |
|---|---|---|---|---|---|---|---|
| 29 | 8 | 8 | 8 | 8 | >64 | >64 | — |
| 36 | 4 | 4 | 4 | 1 | >32 | >32 | >32 |
| 37 | 1 | 1 | 1 | 0.5 | >32 | >32 | >32 |
| 38 | 4 | 4 | 8 | 2 | >32 | >32 | >32 |
| 39 | 0.25 | 0.5 | 0.5 | 0.125 | >32 | >32 | >32 |
| 40 | 1 | 1 | 1 | 0.5 | >32 | >32 | >32 |
| 41 | 2 | 4 | 4 | 1 | >32 | >32 | >32 |
| 42 | 4 | 4 | 4 | 4 | >64 | >64 | — |
| 43 | 0.25 | 0.5 | 0.5 | 0.25 | >32 | >32 | >32 |
| 44 | 2 | 4 | 2 | 2 | >32 | >32 | >32 |
| 46 | 8 | 2 | 4 | 2 | >64 | >64 | >64 |
| 47 | 4 | 2 | 1 | 1 | >64 | >64 | >64 |
| 48 | 4 | 2 | 2 | 1 | >64 | >64 | >64 |
| 59 | 1 | 2 | 1 | 1 | >32 | >32 | >32 |

The compounds of the general formulae (I), (Ia), (Ib), (Ic), (Id), (Ie) and (If) according to the invention have a broad antibacterial spectrum, specifically against Gram-positive bacteria and Mycobacteria, Corynebacteria, *Haemophilus influenzae* and anaerobic germs, coupled with a low toxicity. These properties enable them to be used as chemotherapeutic active compounds in human and veterinary medicine.

The compounds according to the invention are active against a broad spectrum of microorganisms. Gram-positive bacteria and bacteria-like microorganisms, such as Mycoplasma, can be combated and the diseases caused by these pathogens can be prevented, alleviated and/or cured with the aid of the compounds.

The compounds according to the invention are particularly active against bacteria and bacteria-like microorganisms. They are therefore particularly suitable in human and veterinary medicine for prophylaxis and chemotherapy of local and systemic infections caused by such pathogens.

The present invention includes pharmaceutical formulations which, in addition to non-toxic, inert pharmaceutically suitable excipients, comprise one or more compounds according to the invention or which consist of one or more active compounds according to the invention, as well as processes for the preparation of these formulations.

If appropriate, the active compound or compounds can also be in microencapsulated form in one or more of the abovementioned excipients.

The therapeutically active compounds should preferably be present in the abovementioned pharmaceutical formulations in a concentration of about 0.1 to 99.5, preferably about 0.5 to 95% by weight of the total mixture.

In addition to the compounds according to the invention, the abovementioned pharmaceutical formulations can also comprise other pharmaceutical active compounds.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably comprises the active compound or compounds according to the intention in amounts of about 1 to about 80, in particular 3 to 30 mg/kg of body weight.

The new compounds can be combined in the customary concentrations and formulations together with the feed or lactamase inhibitors, for example with penicillins which are particularly resistant to penicillinase and clavulanic acid. Such a combination would be, for example, that with oxacillin or dicloxacillin.

The compounds according to the invention can also be combined with other antibiotics for the purpose of extending the action spectrum and in order to achieve an increase in action.

Appendix to the Experimental Section

List of the Mobile Phase Mixtures used for the Chromatography

| | |
|---|---|
| I | Methylene chloride:methanol |
| II | Toluene:ethyl acetate |
| III | Acetonitrile:water |
| IV | Ethyl acetate |
| V | Petroleum ether:ethyl acetate |

Abbreviations

| | |
|---|---|
| Z | Benzyloxycarbonyl |
| Boc | tert-Butyloxycarbonyl |
| DMF | Dimethylformamide |
| Ph | Phenyl |
| Me | Methyl |
| THF | Tetrahydrofuran |
| CDI | Carbonyldiimidazole |
| DCE | Dichloroethane |

STARTING COMPOUNDS

5-Bromo-2-isocyanato-pyridine hydrochloride

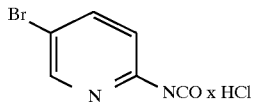

78.0 ml (0.64 mol) of trichloroethyl chloroformate are added dropwise to a stirred solution of 100 g (0.58 mol) of 2-amino-5-bromopyridine in 400 ml of 1,2-dichloroethane at the boiling point. After the addition, the mixture is boiled under reflux for 2 hours and is then allowed to cool to room temperature. The precipitate formed is separated off by filtration, washed thoroughly with 100 ml of 1,2-dichloroethane and dried under a high vacuum over sodium hydroxide. 98.3 g (72%) of the title compound are obtained as a yellow solid.

Melting point: 248°–254° C. (decomposition). $R_f$=0.23 (ethyl acetate). MS (EI) m/z=198 (M)$^+$ As described for Example I, the hydrochlorides of the following isocyanates were obtained from the corresponding heteroaromatic amines by reaction with trichloromethyl chloroformate:

TABLE I

D—N=C=O x HCl

| Ex. No. | D | Yield (% of theory) | Melting Point (°C.) | MS (DCI, NH₃) m/z = (M + H)⁺ |
|---|---|---|---|---|
| II | 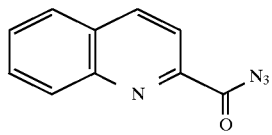 | 90 | >265 | 171 |
| III | 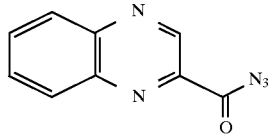 | 75 | 166 | 200 |

EXAMPLE IV

Quinoline-2-carboxylic acid azide 47 ml (0.34 mol) of triethylamine are added to a stirred suspension, cooled to −10° C., of 30.0 g (0.17 mol) of quinoline-2-carboxylic acid in 385 ml of anhydrous tetrahydrofuran, and the mixture is stirred at −10° C. for 10 minutes, whereupon a clear solution forms. 73.0 ml (0.34 mol) of diphenylphosphoryl azide are then added dropwise and the reaction mixture is left to stand in a refrigerator at 0° C. for 20 hours. Thereafter, the mixture is stirred into 350 ml of ice-cold dilute NaHCO₃ solution. The precipitate formed is separated off by filtration, washed with water and dried in air. 88.9 g (86%) of the title compound are obtained as a pale solid.

R$_f$=0.35 (toluene:ethyl acetate 9:1)

EXAMPLE V

Quinoxaline-2-carboxylic acid azide

As described for Example IV, 2.87 g (96%) of the corresponding acid azide are obtained as a brown powder from 2.60 g (15.0 mmol) of quinoxaline-2-carboxylic acid.

R$_f$=0.65 (methylene chloride:ethyl acetate 9:1)

EXAMPLE VI

6-Benzyloxycarbonylamino-quinoline

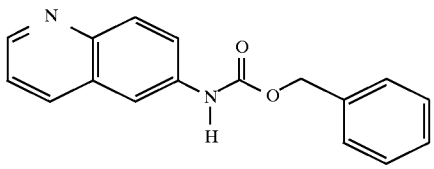

13.0 ml (76.28 mmol) of benzyl chloroformate are added dropwise to a stirred solution, cooled to 0° C. of 10.0 g (69.36 mmol) of 6-aminoquinoline in 160 ml of water and 80 ml of THF in the course of 30 minutes, the pH being kept at 10 by simultaneous addition of a 4N NaOH solution. The mixture is subsequently stirred at 0° C. for a further 2 hours, the THF is evaporated off in vacuo and the residue is extracted with 3×50 ml of ethyl acetate. The combined organic extracts are dried over MgSO₄, the solvent is evaporated off in vacuo and the residue is purified by chromatography over 450 g of silica gel (toluene:ethyl acetate 1:4). 11.60 g (60%) of the title compound are obtained as crystals.

Melting point: 122° C. R$_f$=0.43 (toluene:ethyl acetate 1:4). MS (EI) m/z=278 (M⁺). ¹H-NMR (300 MHz, D$_6$-DMSO): δ=5.22 (s, 2H, CH₂O); 7.3–7.5 (m, 6H, Ph, quinoline-H); 7.78 (dd, J=1.5, 9 Hz, 1H, quinoline-H); 7.96 (d, J=9 Hz, 1H, quinoline-H); 8.17 (d, J=1.5 Hz, 1H, quinoline H-5); 8.25 (d, J=9 Hz, 1H, quinoline-H); 8.77 (m, 1H, quinoline H-2).

As described for Example 6, the compounds listed in Table II were obtained from the corresponding heteroaromatic compounds by reaction with benzyl chloroformate:

TABLE II

| Ex. No. | D | Yield (% of theory) | Melting point: [°C.] | R$_f$/mobile phase (ratio) |
|---|---|---|---|---|
| VII | | 47 | 85 | 0.69 V (1:1) |
| VIII | | 76 | 108 | 0.57 II (9:1) |
| IX | | 48 | | 0.55 V (1:1) |
| X | | 36 | 151 | 0.43 I (9:1) |

TABLE II-continued

| Ex. No. | D | Yield (% of theory) | Melting point: [°C.] | R$_f$/mobile phase (ratio) |
|---|---|---|---|---|
| XI | Br-pyridyl-methyl | 86 | | 0.59 I (100:3) |
| XII | phenyl-pyridazinyl-methyl | 75 | 180 | 0.63 V (1:1) |
| XIII | Cl-pyridazinyl-methyl | 48 | 153 | 0.67 V (1:1) |
| XIV | H$_3$C-quinolinyl | 64 | 231 | 0.3 II (1:1) |
| XV | Br-pyridyl-methyl | 65 | 198 | 0.8 II (1:1) |

EXAMPLE XVI

N-Boc-2-amino-6-bromo-1,8-naphthyridine

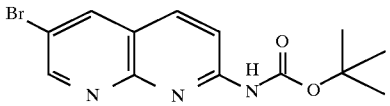

200 mg (0.893 mmol) of 2-amino-6-bromo-1,8-naphthyridine (C. Reichardt; W. Scheibelein, Tetrahedron Lett. 1977, 2087) are dissolved in 3 ml of absolute DMF under argon and the solution is added to a suspension, cooled to 0° C. of 28.2 mg of 80% pure NaH (0.937 mmol) in 2 ml of absolute DMF without the temperature exceeding +5° C. After stirring for 10 minutes, 0.21 g (0.937 mmol) of (Boc)$_2$O is added and the mixture is allowed to come to room temperature overnight. Water is added and the mixture is extracted 3 times with 30 ml of ethyl acetate each time. The organic phase is washed once with 30 ml of water, dried over MgSO$_4$ and evaporated. Column chromatography over silica gel with CH$_2$Cl$_2$:CH$_3$OH=100:2 gives 114 mg (39% of theory) of the title compound as a yellow solid.

R$_f$ value (CH$_2$Cl$_2$:MeOH=100:2): 0.42. Melting point: >230° C.

EXAMPLE XVII

N-Allyl-N-Boc-2-amino-6-bromo-1,8-naphthyridine

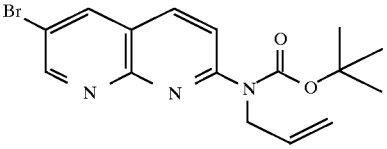

9.7 mg of NaH (80% pure in oil; 0.324 mmol) are suspended in 2 ml of absolute THF under argon and the suspension is cooled to 0° C. A solution of 100 mg (0.308 mmol) of the compound from Example XVI in 3 ml of absolute THF is slowly added and the mixture is subsequently stirred at 0° C. for 10 minutes and at room temperature for a further 15 minutes.

10 mg of tetra-butylammonium iodide and 32 μl (0.37 mmol) of allyl bromide are added and the mixture is stirred overnight at room temperature.

Water is added the mixture is extracted 3 times with 25 ml of ethyl acetate and the extract is dried over MgSO$_4$ and concentrated. The crude product is purified by chromatography over silica gel with CH$_2$Cl$_2$:MeOH=100:1.5. 84 mg (75% of theory) of the title compound are obtained.

R$_f$ value (CH$_2$Cl$_2$:MeOH=100.2): 0.22. Melting point: 114° C.

EXAMPLE XVIII 3-(6-Bromo-1,8-naphthyridine-2-yl)-5-iodomethyl-2-(tert-butyloxy)-oxazoliniumiodide

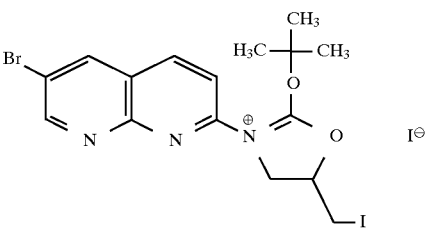

74 mg (0.203 mmol) of the compound from Example XVII are dissolved in 5 ml of chloroform under argon in a darkened flask. 129 mg (0.508 mmol) of iodine are added and the mixture is stirred overnight.

5 ml of 20% strength sodium thiosulphate solution are added, and the organic phase is separated off and concentrated. The residue is stirred with water, filtered off with suction and washed with water.

The residue is dried under a high vacuum to give 99 mg of product.

Melting point: 210° C., with decomposition. $^{13}$C-NMR (DMSO, 75 MHz): 156.2 (d); 153.2(s); 148.3 (s); 148.2 (d); 142.5 (s); 141.1 (d); 120.5 (s); 118.5 (d); 113.6 (d); 86.5 (s); 59.0 (d); 52.6 (t); 27.4 (q); 7.9 (t); MS (FAB): 492 (62), 490 (50), 436 (100).

PREPARATION EXAMPLES

Example 1

(5R)-3-(5-Bromo-pyridin-2-yl)-5-butyryloxy-methyl-oxazolidin-2-one

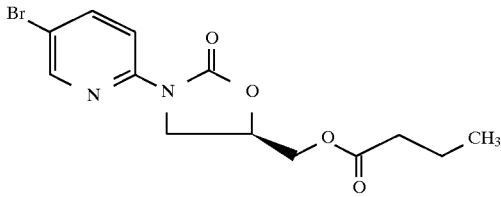

A suspension of 2.17 g (25 mmol) of lithium bromide and 5.46 g (25 mmol) of tributylphosphine oxide in 73 ml of xylene is boiled for 1 hour using a water separator. A mixture of 58.5 ml (0.42 mol) of triethylamine and 66.6 g (0.42 mol) of (R)-glycidyl butyrate is added dropwise at the boiling point. At the same time, 98.2 g (0.42 mol) of the compound from Example 1 are added in portions in the course of 20 minutes. When the addition has ended the mixture is subsequently stirred under reflux for a further hour. It is allowed to cool to room temperature and the solvent is evaporated off in vacuo. Chromatography of the residue over 1 kg of silica gel (toluene:ethyl acetate 95:5) gives 37.9 g (26%) of the title compound as an oil.

$R_f$=0.43 (toluene:ethyl acetate 4:1). MS (FAB) m/z=343 (M+H)$^+$. $^1$H-NMR. (250 MHz, D$_6$-DMSO): δ=0.81 (t, J=7 Hz, 3H, CH$_3$CH$_2$); 1.5 (m, 2H, CH$_3$CH$_2$CH$_2$CO); 2.29 (t, J=7 Hz, 2H, CH$_3$CH$_2$CH$_2$CO); 3.91 (dd, J=7 Hz, 10 Hz, 1H, H-4 trans); 4.25 (dd, J=9 Hz, 10 Hz, 1H, H-4 cis); 4.36 (m, 2H, CH$_2$O); 4.97 (m, 1H, H-5); 8.08 (d, J=1 Hz, 2H, pyridyl H-3,4); 8.50 (d, J=1 Hz, pyridyl H-6).

Example 2

(5R)-3-(quinoline-2-yl)-5-butyryloxymethyl-oxazolidin-2-one

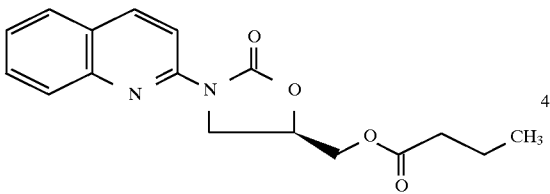

A suspension of 51 mg (0.06 mmol) of lithium bromide and 126 mg (0.06 mmol) of tributylphosphine oxide in 10 ml of 1,3-dichlorobenzene is boiled for 1 hour using a water separator. A mixture of 1.42 ml (10.0 mmol) of (R)-glycidylbutyrate and 19.82 g (10.0 mmol) of the acid azide from Preparation Example IV in 17 ml of 1,3-dichlorobenzene is added dropwise at the boiling point (bath at 220° C.) in the course of 10 minutes (vigorous evolution of gas!). When the addition has ended, the mixture is subsequently stirred under reflux for a further 30 minutes and is then allowed to cool to room temperature. The solvent is evaporated off under a high vacuum and the residue is purified by chromatography over 175 g of silica gel (toluene:ethyl acetate 9:1). 2.51 g (80%) of the title compound are obtained as a pale oil.

$R_f$=0.20 (methylene chloride). $R_f$=0.34 (toluene:ethyl acetate 9:1). MS (FAB) m/z=315 (M+H)$^+$. $^1$H-NMR (250 MHz, CD$_3$OD) δ=0.82 (t, J=7 Hz, 3H, CH$_3$CH$_2$); 1.57 (m, 2H, CH$_3$CH$_2$CH$_2$CO); 2.29 (t, J=7 Hz, 2H, CH$_3$CH$_2$CH$_2$CO); 4.25 (dd, J=6.5, 10 Hz, 1H, H-4 trans); 4.4–4.5 (m, 3H, H-4, CH$_2$O); 5.00 (m, 1H, H-5); 7.48 (m, 1H, H arom); 7.68 (m, 1H, H arom); 7.83 (d, J=7 Hz, 2H, quinoline H-6,7); 8.25 (d, J=8 Hz, 1H, quinoline H-3); 8.36 (d, J=8 Hz, 1H, quinoline H-4).

Example 3

(5R)-3-(Quinolin-6-yl)-5-hydroxymethyl-oxazolidin-2-one

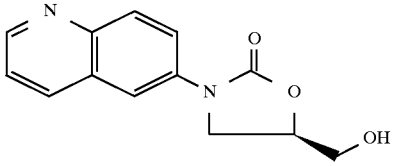

4.70 ml (11.78 mmol) of a 2.5M solution of n-butyllithium in n-hexane are slowly added to a stirred solution, cooled to −78° C., of 3.28 g (11.78 mmol) of 6-benzyloxycarbonylamino-quinoline and 1 mg of 1,10-phenanthroline hydrate in 30 ml of anhydrous THF until the colour changes. Thereafter, 1.67 ml (11.78 mmol) of (R)-glycidyl butyrate are added dropwise and the reaction mixture is allowed to warm to room temperature in the course of 16 hours. 30 ml of saturated aqueous NH$_4$Cl solution are then added dropwise in the course of 15 minutes. The aqueous phase is extracted with 3×60 ml of ethyl acetate and the organic phases are combined, washed with 2×50 ml of NaCl solution and dried over MgSO$_4$. Evaporation of the solvent in vacuo, tritration of the residue with ether and recrystallization from 25 ml of ethanol gives 1.30 g (45%) of the title compound as colourless crystals.

Melting point: 165° C. $R_f$=0.08 (toluene:ethyl acetate 1:4). MS (DCI, NH$_3$) m/z=245 (M+H)$^+$. 1H-NMR (250 MHz, D6-DMSO) δ=3.6–3.8 (m, 2H, CH$_2$O); 4.00 (dd, J=7, 10 Hz, 1H, H-4 trans); 4.25 (dd, J=10, 10 Hz, 1H, H-4 cis); 4.78 (m, 1H, H-5); 5.25 (t, J=6 Hz, 1H, OH); 7.52 (dd, J=6, 9 Hz, 1H, quinoline H-3); 7.92 (d, J=1.5 Hz, 1H, quinoline H-5); 8.02 (d, J=10 Hz, 1H, quinoline H-8); 8.3 (m, 2H, quinoline H-4,7); 8.82 (m, 1H, quinoline H-2).

Example 4

(5R)-3-(5-bromo-pyridin-2-yl)-5-hydroxymethyl-oxazolidin-2-one

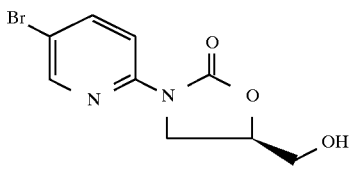

185 mg (0.57 mmol) of caesium carbonate are added to a solution of 19.6 g (57.3 mmol) of the compound from Example 1 in 125 ml of anhydrous methanol and the mixture is stirred at room temperature for 5 hours. The solvent is evaporated off in vacuo and the residue is stirred with 30 ml of ether. the precipitate is separated off by filtration, rehashed with 25 ml of water and 5 ml of ether and dried under a high vacuum. 10.73 g (69%) of the title compound are obtained as pale crystals.

Melting point: 123°–124° C. $R_f$ value: 0.09 (toluene:ethyl acetate 4:1). MS (DCI, NH$_3$) m/z=273 (M+H)$^+$. $^1$H-NMR (200 MHz, CD$_3$OD) δ=3.68 (d, J=5.9 Hz, 1 H, CH$_2$O); 3.87 (dd, J=4, 9 Hz, 1H, CH$_2$O); 4.06 (dd, J=7, 10 Hz, 1H, H-4 trans); 4.26 (dd, J=9, 10 Hz, 1H, H-4 cis); 4.75 (m, 1H, H-5); 7.92 (dd, J=1.5 Hz 10 Hz, 1H, pyridyl H-3); 8.12 (d, J=10 Hz, 1H, pyridyl H-4); 8.40 (d, J=1.5 Hz, 1H, pyridyl H-6).

TABLE 1

| Ex. No. | D | analogous preparation method (reagent) | Yield [% of theory] | Melting point [°C.] | R$_f$/mobile phase (ratio) | MS (FAB) m/z (M + H)$^+$ |
|---|---|---|---|---|---|---|
| 5 | quinoline | 4 (Cs$_2$CO$_3$) | 63 | 159 | 0.28, II (1:1) | 245 |
| 6 | quinoxaline | 4 (Cs$_2$CO$_3$) | 29 | 174 | 0.44, II (0:100) | 246 |
| 7 | Br-pyrimidine | 4 (NaHCO$_3$) | 5 | amorphous | 0.20, II (1:1) | 274 |
| 8 | Br-pyridine | 3 (BuLi) | 60 | 185–187 | 0.34, I (100:5) | 272 |
| 9 | Br-pyrazine | 3 (BuLi) | 12 | – | 0.19 II (1:1) | 274 |
| 10 | H$_3$C-pyridine | 3 (BuLi) | 78 | 144 | 0.32 I (95:5) | 209 |
| 11 | Br-methylquinoline | 3 (BuLi) | 86 | 205 with decomp. | 0.25 I (100:5) | |
| 12 | Br, CH$_3$-pyridine | 3 (BuLi) | 1 | 107 | 0.18 II (7:3) | 287 |
| 13 | C$_6$H$_5$-pyridazine | 3 (BuLi) | 28 | 158 | 0.29 II (1:1) | 218 |
| 14 | Cl-pyridazine | 3 (BuLi) | 19 | 121 | 0.22 II (1:1) | 230 |

Example 15

(5R)-3-(5-Bromo-pyridin-2-yl)-5-methanesulphonyloxy-methyl-oxazolidin-2-one

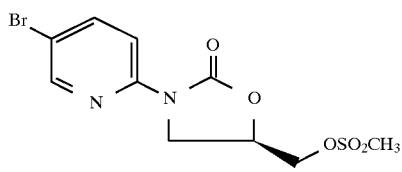

3.27 ml (42.28 mmol) of methanesulphonyl chloride are slowly added to a stirred solution, cooled to 0° C., of 10.5 g (38.44 mmol) of the compound from Example 4 and 6.40 ml (46.14 mmol) of triethylamine in 36 ml of anhydrous methylene chloride. The mixture is subsequently stirred at 0°–5° C. for 10 minutes and stirred into 50 ml of ice-water. The organic base is separated off, washed with 20 ml of saturated NaHCO$_3$ solution and 20 ml of ice-water and dried over MgSO$_4$. The solvent is evaporated in vacuo and the residue is stirred with 50 ml of ether, filtered off with suction and dried under a high vacuum. 12.8 g (95%) of the title compound are obtained as colourless crystals.

Melting point: 138°–138.5° C. $R_f$=0.65 (methylene chloride:methanol 95:5). MS (DCI, NH$_3$) m/z=351 (M+H)$^+$. $^1$H-NMR (250 MHz, D$_6$-DMSO) δ=3.25 (s, 3H, OSO$_2$CH$_3$); 3.91 (dd, J=7, 10 Hz, 1H, H-4 trans); 4.27 (dd, J=10, 10 Hz, 1H, H-4 cis); 4.52 (m, 2H, CH$_2$O); 5.02 (m, 1H H-5); 8.09 (s, 2H, pyridyl H-3,4); 8.52 (s, 1H, pyridyl H-6).

As described for Example 15, the following methanesulphonates are obtained from the corresponding alcohols (Table 2):

Example 19

(5R)-3-(5-Bromo-pyridin-2-yl)-5-azidomethyl-oxazolidin-2-one

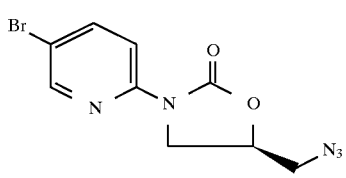

3.01 g (46.28 mmol) of sodium azide are added to a stirred solution of 12.5 g (35.6 mmol) of the compound from Example 15 in 48 ml of anhydrous DMF and the mixture is stirred at 70° C. for 3 hours. It is allowed to cool to room temperature and is stirred into 100 ml of ice-water. The resulting precipitate is separated off by filtration, washed with 50 ml of water and 20 ml of petroleum ether and dried in air. 10.1 g (95%) of the title compound are obtained as pale crystals.

Melting point: 64°–67° C. $R_f$=0.63 (toluene:ethyl acetate 2:3). MS (DCI, NH$_3$) m/z=298 (M+H)$^+$. $^1$H-NMR (250 MHz, D$_6$-DMSO) δ=3.73 (m, 2H, CH$_2$N$_3$); 3.87 (dd, J=6, 8 Hz, 1H, H-4 trans); 4.22 (dd. J=8, 8 Hz, 1H, H-4 cis); 4.92 (m, 1H, H-5); 8.08 (s, 2H pyridyl H-3,4); 8.51 (s, 1H, pyridyl H-6).

As described for Example 19, the following azides are obtained from the corresponding methanesulphonates (Table 3):

TABLE 2

| Ex. No. | D | Yield [% of theory] | melting point [°C.] | R$_f$/mobile phase (ratio) | MS (FAB) m/z (M + H)$^+$ |
|---|---|---|---|---|---|
| 16 | (2-quinolinyl) | 98 | 158 | 0.42, II (I:1) | 323 |
| 17 | (6-methyl-quinoline-N) | 73 | 143 | 0.14, II (1:9) | 323 |
| 18 | (2-bromo-4-methyl-pyridyl) | 95 | – | 0.32, I (100:3) | |

TABLE 3

D—N(C=O)O-CH(CH2N3)-CH2- (oxazolidinone with azidomethyl)

| Ex. No. | D | Yield [% of theory] | Melting point [°C.] | R_f/mobile phase (ratio) | MS (FAB) m/z (M + H)+ |
|---|---|---|---|---|---|
| 20 | quinolin-2-yl | 98 | 107 | 0.56, II (4:1) | 270 |
| 21 | quinolin-6-yl | 89 | 92 | 0.20, II (1:9) | 270 |
| 22 | 5-Bromo-pyridin-2-yl | 82 | 80 | | 298 |

Example 23

(5S)-3-(5-Bromo-pyridin-2-yl)-5-aminomethyl-oxazolidin-2-one hydrochloride

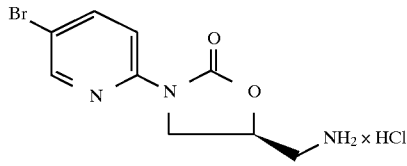

A stirred solution of 10.1 g (33.9 mmol) of the compound from Example 19 in 16.5 ml of 1,2-dimethoxyethane is heated to 50° C. 4.68 ml (4.70 mmol) of trimethylphosphite are slowly added dropwise (evolution of gas), and after the addition has ended the mixture is subsequently stirred at 90° C. for 2 hours. 6.6 ml of 6N HCl are now added dropwise and the mixture is subsequently stirred again at 90° C. for 2 hours. It is allowed to cool to room temperature and the precipitate is separated off by filtration, washed with 2×10 ml of 1,2-dimethoxyethane and dried under a high vacuum over NaOH. 8.9 g (85%) of the title compound are obtained as colourless crystals.

Melting point: 260°–262° C. R_f=0.53 (acetonitrile:water 4:1). MS (EI) m/z=271 (M+). $^1$H-NMR (250 MHz, D$_6$-DMSO) δ=3.28 (m, 2H, C$\underline{H}_2$NH$_2$); 3.93 (dd, J 7, 9 Hz, 1H, H-4 trans); 4.28 (dd, J=9, 9 Hz, 1H, H-4 cis); 5.00 (m, 1H, H-5); 8.05 (s, 2H, pyridyl H-3,4); 8.5 (m, 3H, NH$_2$, pyridyl H-6).

As described for Example 23, the following products are obtained by reaction of the corresponding azides (Table 4):

TABLE 4

D—N(C=O)O-CH(CH2NH2·HCl)-CH2- (oxazolidinone with aminomethyl·HCl)

| Ex. No. | D | Yield [% of theory] | Melting point [°C.] | R_f/mobile phase (ratio) | MS (FAB) m/z (M + H)+ |
|---|---|---|---|---|---|
| 24 | quinolin-2-yl | 62 | 216 | 0.54, II (4:1) | 243$^{a)}$ |
| 25 | quinolin-6-yl | 87 | 80 | 0.12, II (4:1) | 244 |

TABLE 4-continued

![structure: D—N-C(=O)-O-CH-CH2-NH2 x HCl on oxazolidinone ring]

| Ex. No. | D | Yield [% of theory] | Melting point [°C.] | R_f/mobile phase (ratio) | MS (FAB) m/z (M + H)+ |
|---|---|---|---|---|---|
| 26 | Br-pyridin-2-yl (5-methyl) | 79 | | 0.13, I (100:3) | — | a) MS (EI) m/z = (M+)

Example 27

(5S)-3-(5-Bromo-pyridin-2-yl)-5-acetylaminomethyl-oxazolidin-2-one

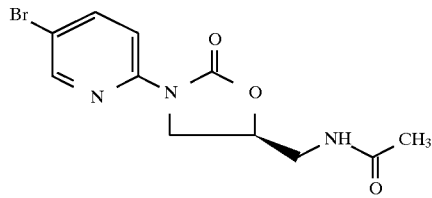

A solution of 1.03 g (25.73 mmol) of sodium hydroxide in 8.4 ml of water is added to a stirred solution of 8.90 g, (28.84 mmol) of the compound from Example 23 in 35 ml of THF. 2.68 ml (28.30 mmol) of acetic anhydride in 3 ml of THF are slowly added dropwise at 0°–5° C., and the pH is kept at 9 by simultaneous addition of a 5N aqueous NaOH solution. The mixture is subsequently stirred at 0° C. for 1 hour and the solvent is evaporated off in vacuo. The residue is stirred thoroughly with 2×20 ml of water, separated off and dried under a high vacuum with Sicapent. 8.90 g (98%) of the title compound are obtained as colourless crystals.

Melting point: 166°–168° C. $R_f$=0.57 (acetonitrile:water 95:5). MS (EI) m/z=313 (M+). $^1$H-NMR (250 MHz, D$_6$-DMSO) δ=1.82 (s, 3H, COCH$_3$); 3.42 (t, J=6, 5 Hz, 2H, CH$_2$N); 3.84 (dd, J=7, 9 Hz, 1H, H-4 trans); 4.18 (dd, J=9, 10 Hz, 1H, H-4 cis); 4.75 (m, 1H, H-5); 8.05 (s, 2H, pyridyl H-3,4); 8.23 (m, 1H, NHCO); 8.50 (s, 1H, pyridyl H-6).

As described for Example 27, the following products are obtained by acylation of the corresponding amines (Table 5):

TABLE 5

![structure: D—N-oxazolidinone-CH2-NH-C(=O)-CH3]

| Ex. No. | D | Yield [% of theory] | Melting point [°C.] | R_f/mobile phase (ratio) | MS (FAB) m/z (M + H)+ |
|---|---|---|---|---|---|
| 28 | quinolin-2-yl | 80 | 187 | 0.44, I (9:1) | 286 |
| 29 | quinolin-6-yl | 42 | 146 | 0.33, I (9:1) | 286 |
| 30 | quinoxalin-2-yl | 94 | 242 | 0.58 III (9:1) | 286 a) |
| 31 | 5-Bromo-pyridin-2-yl (methyl) | 56 | 133 | 0.22 I (100:5) | |

TABLE 5-continued

|  |  | Yield | Melting | R_f/mobile | MS (FAB) |
|---|---|---|---|---|---|
| Ex. No. | D | [% of theory] | point [°C.] | phase (ratio) | m/z (M + H)+ |
| 32 | (6-methylquinolin-2-yl with H₃C at 3-position) | 15 | 153 with decomp. | 0.33 II (1:1) | |
| 33 | (3-bromo-6-methylquinolin-2-yl) | 90 | 202 | — | 365 |

Example 34 and Example 35

(5S)-3-(6-Bromo-quinolin-2-yl)-5-acetaminomethyl-oxazolidin-2-one and (5S)-3-(8-bromo-quinolin-2-yl)-5-acetaminomethyl-oxazolidin-2-one

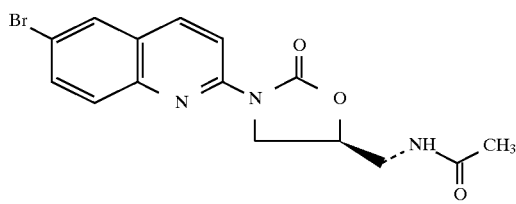
(34)

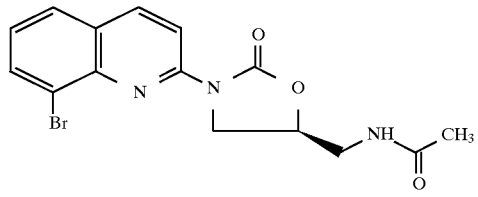
(35)

4.36 g (19.73 mmol) of silver trifluoroacetate are added to a stirred solution, cooled to 0° C., of 4.38 g (15.20 mmol) of the compound from Example 28 in 87 ml of chloroform and 56 ml of acetonitrile. Thereafter, 0.78 ml (15.20 mmol) of a standard solution of bromine in chloroform is added dropwise in the course of 15 minutes. The ice bath is removed and the mixture is subsequently stirred at room temperature for 4 hours. For working up, the mixture is stirred into 100 ml of ethyl acetate and washed with 2×50 ml of saturated $NaHCO_3$ solution and 50 ml of NaCl solution, and the organic phase is dried over $MgSO_4$. The solvent is evaporated off in vacuo and the residue is stirred with 50 ml of ether/n-pentane. The precipitate is separated off by filtration and dried under a high vacuum. 5.43 g (98%) of the title compound are obtained as a mixture of the isomers. Separation of this mixture over 540 g of silica gel (ethyl acetate) gave 2.70 g (43%) of the non-polar 8-bromo isomer as colourless crystals, Melting point: 211° C. $R_f$=0.29 (ethyl acetate). MS (DCI, $NH_3$ m/z=364 (M+H)+. ¹H-NMR (250 MHz, $D_6$-DMSO) δ=1.85 (s, 3H, $COCH_3$); 3.50 (m, 2H, $CH_2$NH); 4.01 (dd, J=7, 10 Hz, 1H, H-4 trans); 4.45 (dd, J=9, 10 Hz, 1H, H-4 cis); 4.85 (m, 1H, H-5); 7.45 (t, J=7 Hz, 1H, quinoline H-6); 7.99 (dd J=1, 7 Hz, 1H, quinoline H-7): 8.11 (dd, J=1, 7 Hz, 1H, quinoline H-5); 8.29 (m, 1H, NHCO); 8.43 (m, 2H, quinoline H-3,4). and 1.02 g (16%) of the polar 6-bromo isomer, melting point: 210°–213° C.

$R_f$=0.22 (ethyl acetate). MS (DCI, $NH_3$) m/z=364 (M+H) +. ¹H-NMR (250 MHz $D_6$-DMSO) δ=1.85 (s, 3H, $COCH_3$); 3.48 (m, 2H, $CH_2$N); 4.00 (dd, J=6, 10 Hz, 1H, H-4 trans); 4.36 (dd, J=9, 10 Hz, 1H, H-14 cis); 4.80 (m, 1H, H-5); 7.8 (m, 2H, quinoline H-7,8); 8.21 (d, J=1 Hz, 1H, quinoline H-5); 8.27 (m, 1H, NHCO); 8.37 (s, 2H, quinoline H-3,4). and 830 mg (13%) of a mixed fraction of the two isomers.

Example 36

(5S)-3-[5-(4-Methylphenyl)pyridin-2-yl]-5-acetyl-aminomethyl-oxazolidin-2-one

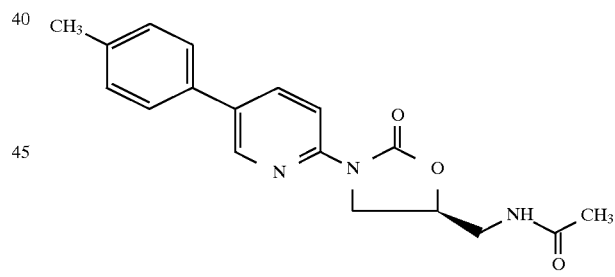

104 mg (0.09 mmol) of tetrakis(triphenylphosphine) palladium are added to a stirred solution of 943 mg (3.00 mmol) of the compound from Example 27 and 530 mg (3.90 mmol) of 4-methylphenyl-boronic acid in 15.4 ml of THF and the mixture is heated under reflux for 1 hour. Thereafter, 2.07 ml (4.14 mmol) of a 2M $Na_2CO_3$ solution are added and the mixture is heated under reflux for 30 hours. The mixture is then allowed to cool, the solvent is evaporated off in vacuo and the residue is purified by chromatography over 88 g of silica gel (ethyl acetate). Recrystallization from methanol gives 582 mg (60%) of the title compound as colourless crystals.

Melting point: 186°–188° C. $R_f$=0.18 (ethyl acetate). MS (EI) m/z=325 (M)+. ¹H-NMR (200 MHz $D_6$-DMSO) δ=1.85 (s, 3H, $COCH_3$); 2.36 (s, 3H, $CH_3$); 3.45 (m, 2H, $CH_2$N); 3.91 (dd J=7, 10 Hz 1H, H-4 trans); 4.25 (dd, J=10, 10 Hz, 1H, H-4 cis); 4.77 (m, 1H, H-5); 7.30, 7.61 (AB, $J_{AB}$=9 Hz, 4H, tolyl-H); 8.15 (s, 2H, pyridyl H-3,4); 8.28 (bt, J=6 Hz, 1H, NHCO); 8.68 (m, 1H, pyridyl H-6).

The compounds listed in Tables 6 and 7 are prepared analogously to the instructions of Example 36:

TABLE 6

| Ex. No. | D | Yield (% of theory) | Melting point (°C.) | $R_f$(Ethyl acetate) | MS(FAB) m/z (M + H)$^+$ |
|---|---|---|---|---|---|
| 37 | phenyl | 42 | 145 | 0.20 | 312 |
| 38 | 2-CHO-phenyl | 65 | 70 | 0.16 | 340 |
| 39 | 3-CHO-phenyl | 57 | 162 | 0.17 | 340 |
| 40 | 4-CHO-phenyl | 54 | 120 | 0.15 | 340 |
| 41 | 4-acetyl-phenyl | 29 | 221.5 | 0.11 | 354 |
| 42 | 3-acetyl-phenyl | 60 | 154 | 0.10 | 354 |
| 43 | 5-acetyl-thien-2-yl | 31 | 223 | 0.10 | 360 |
| 44 | 5-CHO-thien-2-yl | 30 | 185 | 0.10 | 346 |

TABLE 6-continued

| Ex. No. | D | Yield (% of theory) | Melting point (°C.) | $R_f$(Ethyl acetate) | MS(FAB) m/z (M + H)$^+$ |
|---|---|---|---|---|---|
| 45 | 3-propionyl-phenyl | 65 | 193 | 0.18 | 368 |
| 46 | 3-Cl-4-F-phenyl | 11 | 139 | 0.19 | 364 |
| 47 | 4-F-phenyl | 63 | 153 | 0.17 | 330 |
| 48 | 3-NO$_2$-phenyl | 52 | 118 | 0.15 | 357 |
| 49 | (E)-propenyl-phenyl | 49 | 189 | 0.17 | 338 |
| 50 | 3,5-bis(CF$_3$)-phenyl | 33 | 186 | 0.25 | 448 |
| 51 | 4-CH$_3$O-phenyl | 50 | 180 | 0.14 | 342 |
| 52 | pyridin-3-yl | 46 | — | 0.33 I (9:1) | 313 |

TABLE 7

[Structure: quinoline with R' at 6-position and R'' at 8-position, connected to oxazolidinone with CH2-NHC(O)CH3 side chain]

| Ex. No. | R' | R'' | Yield (% of theory) | Melting point (°C.) | $R_f$ (Ethyl acetate) | MS (DCI, $NH_3$) m/z $(M + H)^+$ |
|---|---|---|---|---|---|---|
| 53 | CH₃CO-thiophene-yl | H | 37 | 245 | 0.15 | 410 |
| 54 | 3-CHO-phenyl | H | 33 | 236 | 0.19 | 390 |
| 55 | 4-CH₃-phenyl | H | 44 | 232 | 0.23 | 376 |
| 56 | H | 3-CHO-phenyl | 79 | Foam | 0.25 | 390 |
| 57 | H | 3,5-(CF₃)₂-phenyl | 47 | 208 | 0.54 | 498[a] |
| 58 | H | CH₃CO-thiophene-yl | 55 | 235 | 0.16 | 410 |
| 59 | H | 4-CH₃-phenyl | 48 | 186 | 0.35 | 376 |
| 60 | 4-(H₃C-C(O))-phenyl | H | 36 | 212 | 0.29 | 404 |

[a] MS (FAB) m/z = $(M + H)^+$

Example 61

(5S)-3-[5-(2-Hydroxymethyl-phenyl)-pyridin-2-yl]-
5-acetyl-aminomethyl-oxazolidin-2-one

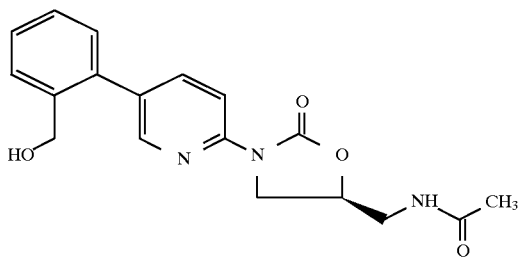

8 mg (0.20 mmol) of sodium borohydride are added to a stirred solution, cooled to 0° C., of 88 mg (0.26 mmol) of the compound from Example 38 in 3 ml of methanol, and the mixture is stirred at 0° C. for 4 hours. The solvent is evaporated off in vacuo and the residue is purified by chromatography over 9 g of silica gel (ethyl acetate). 25 mg (27%) of the title compound are obtained as colourless crystals.

Melting point from 85° C. decomposition. $R_f$=0.06 (ethyl acetate). MS (DCI, $NH_3$) m/z=342 (M+H)$^+$. $^1$H-NMR (250 MHz, $D_6$-DMSO) δ=1.86 (s, 3H, $COCH_3$); 3.46 (m, 2H, $CH_2N$); 4.02. (dd, J=8, 10 Hz, 1H, H-4 trans); 4.28 (dd, J=10, 10 Hz, 1H, H-4 cis); 4.40 (d, J=6 Hz, 2H, $CH_2O$); 4.76 (m, 1H, H-5); 5.21 (t, 1H, OH); 7.3–7.6 (m, 4H, H aromatic); 8.91 (dd, J=1.5 9 Hz, 1H, pyridyl H-4); 8.12 (d, J=9 Hz, 1H, pyridyl H-3); 8.27 (m, 1H, CONH); 8.40 (d, J=1.5 Hz, 1H, pyridyl H-6).

Example 62

(5S)-3-(Quinoline-6-yl)-5-acetylaminomethyl-
oxazolidin-2-one hydrochloride

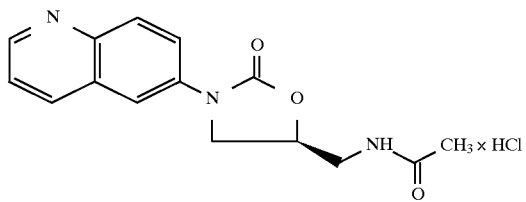

5 ml of a 1N solution of gaseous hydrogen chloride in ether are added dropwise to a stirred solution of 285 mg (1.00 mmol) of the compound from Example 29 in 5 ml of anhydrous dioxane. The mixture is subsequently stirred at room temperature for 30 minutes, 20 ml of ether are added, the mixture is stirred thoroughly and the precipitate is separated off by filtration. The precipitate is dissolved in 30 ml of water and the solution is forced through a "Millipore membrane" (0.2μ) and freeze dried. 300 mg (93%) of the title compound are obtained as a colourless lyophilisate, and dried under a high vacuum over NaOH.

$^1$H-NMR (300 MHz, $D_2O$) δ=2.02 (s, 3H, $COCH_3$); 3.71 (m, 2H, $CH_2N$); 4.15 (dd, J=10 Hz, 1H, H-4 trans); 4.43 (dd, J=10, 10 Hz, 1H, H-4 cis); 5.02 (m, 1H, H-5); 8.07 (dd, J=6, 9 Hz, 1H, quinoline H-3); 8.16 (d, J=1 Hz, 1H, quinoline H-5); 8.23 (d, J=10 Hz, 1H, quinoline H-8); 8.50 (dd, J=1, 10 Hz, 1H, quinoline H-7); 9.05 (m, 2H, quinoline H-2, 4).

Example 63

(5S)-3-(1-Methyl-quinoline-6-yl)-5-
acetylaminomethyl-oxazolidin-2-one iodide

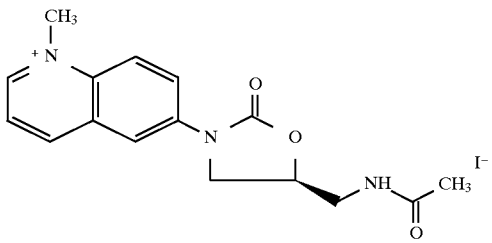

0.35 ml (5.05 mmol) of iodomethane is added to a stirred solution of 314 mg (1.10 mmol) of the compound from Example 29 in 3 ml of anhydrous acetonitrile and the mixture is stirred at room temperature for 2 hours, whereupon a pale precipitate forms. 50 ml of ether are added, the mixture is stirred thoroughly for 10 minutes and the precipitate is separated off by filtration, washed with 5 ml of ether and dried under a high vacuum. 451 mg (96%) of the title compound are obtained as pale crystals.

Melting point: 196° C. with decomposition. $R_f$=0.06 (acetonitrile/water 4:1). MS (FAB): 300 (M$^+$, 100) free cation. $^1$H-NMR ($D_6$-DMSO, TMS): 9.4 (d, J=6 Hz, 1H); 9.22 (d, J=8 Hz, 1H); 8.7 (dd, J=12 Hz, J=3 Hz, 1H); 8.56 (d, J=12 Hz, 1H); 8.25–8.4 (m, 2H); 8.15 (dd, J=8 Hz, J=6 Hz, 1H); 4.8–4.95 (m, 1H); 4.62 (s, 3H); 4.33 (t, J=10 Hz, 1H); 3.95 (dd, J=10 Hz, J=7 Hz, 1H); 3.45–3.57 (m, 2H); 1.83 (s, 3H).

The compounds listed in Table 8 are prepared as described for Example 63:

TABLE 8

| Ex. No. | R— | X | Yield (%) | Melting point (°C.) | $R_f$, mobile phase (ratio) | MS (FAB) m/z (M)$^+$ |
|---|---|---|---|---|---|---|
| 64 | $C_2H_5$ | I | 59 | 76 | 0.06, III (4:1) | 314 |

Example 65

(5R)-3-(Quinoline-6-yl)-5-acetylaminomethyl-oxazolidin-2-one N-1-oxide

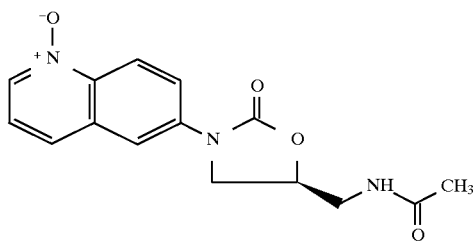

832 mg (3.85 mmol) of 80% strength n-chloroperbenzoic acid are added to a stirred solution of 500 mg (1.75 mmol) of the compound from Example 29 in 5 ml of methylene chloride and the mixture is stirred at room temperature for 16 hours. Thereafter, the reaction mixture is stirred into 20 ml of 10% strength aqueous $Na_2SO_3$ solution. The aqueous phase is separated off and evaporated in vacuo. 25 ml of toluene and 1.5 g of silica gel are added and the mixture is evaporated again. The residue is purified by chromatography over 50 g of silica gel (methylene chloride:methanol 4:1). the product-containing fractions are combined, and 200 ml of ether are added. The resulting precipitate is separated off by filtration and dried under a high vacuum. 453 mg (86%) of the title compound are obtained as colourless crystals.

Melting point: 191° C. (decomposition). $R_f$=0.15 (methylene chloride:methanol 9:1). MS (FAB) m/z=302 $(M+H)^+$. $^1$H-NMR (300 MHz, $D_6$-DMSO): δ=1.85 (s, 3H, $COCH_3$); 3.50 (m, 2H, $CH_2N$); 3.91 (dd, J=7, 10 Hz, 1H, H-4 trans); 4.28 (dd, J=10, 10 Hz, 1H, H-4 cis); 4.82 (m, 1H, H-5); 7.3–7.5 (m, 2H); 7.9 (m, 1H); 8.0 (s, 1H, quinoline H-5); 8.3 (m, 1H); 8.50 (m, 1H, quinoline H-2).

The compounds listed in Table 9 are prepared analogously to the instructions of Example 15

TABLE 9

| Ex. No. | D | Yield (% of theory) | Melting point (°C.) | $R_f$/mobile phase (ratio) | MS(FAB) m/z (M + H)$^+$ |
|---|---|---|---|---|---|
| 66 | quinoxalin-2-yl | 93 | 164 | 0.3 II (1:1) | 324 |
| 67 | 5-bromopyrimidin-2-yl | | | | |
| 68 | 6-methylpyridin-2-yl | 96 | Oil | 0.43 II (2:3) | 287 |
| 69 | 6-bromoquinolin-2-yl | 22 | — | — | — |
| 70 | 6-methylquinolin-2-yl | 39 | — | — | — |
| 71 | 5-bromo-6-methylpyridin-2-yl | 53 | 118 | 0.27 IV (7:3) | 365 |
| 72 | 6-phenylpyridazin-3-yl | 63 | 222 | 0.22 II (1:1) | 350 |

The compounds listed in Table 10 are prepared analogously to the instructions of Example 19

TABLE 10

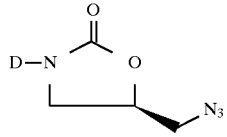

| Ex. No. | D | Yield (% of theory) | Melting point (°C.) | $R_f$/mobile phase (ratio) | MS(FAB) m/z (M + H)$^+$ |
|---|---|---|---|---|---|
| 73 | 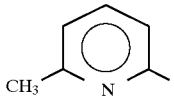 | 80 | — | 0.80 I (95:5) | 233 |
| 74 | 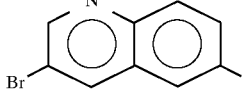 | 50 | — | 0.28 II (1:1) | — |
| 75 | 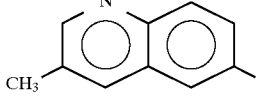 | 28 | — | 0.12 II (1:1) | — |
| 76 | 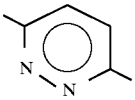 | 96 | 144 | 0.60 IV | 297 |
| 77 | 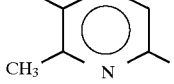 | — | — | — | — |
| 78 | 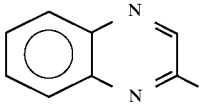 | 88 | 103 | 0.35 II (1:1) | 270[a] |

[a] MS(EI) m/z = M$^+$

The compounds listed in Table 11 are prepared analogously to the instructions of Example 23

TABLE 11

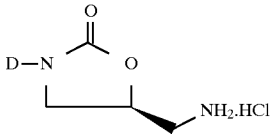

| Ex. No. | D | Yield (% of theory) | Melting point (°C.) | $R_f$/mobile phase (ratio) | MS(FAB) m/z (M + H)$^+$ |
|---|---|---|---|---|---|
| 79 | 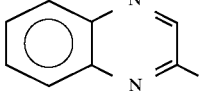 | 83 | 253 | 0.28 III (4:1) | 224[a] |
| 80 | 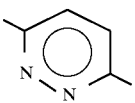 | 75 | 273 | 0.24 III (4:1) | 271 |

TABLE 11-continued

D—N(=O)—O—[ring]—NH₂·HCl

| Ex. No. | D | Yield (% of theory) | Melting point (°C.) | R_f/mobile phase (ratio) | MS(FAB) m/z (M + H)+ |
|---|---|---|---|---|---|
| 81 | 3-methyl-7-quinolinyl (CH₃ on left ring) | 98 | — | — | — |
| 82 | 3-bromo-7-quinolinyl | 75 | — | — | — |
| 83 | 6-methyl-pyridin-2-yl | 75 | — | 0.21 III (9:1) | 207[a] |

[a] MS(EI) m/z = M+

The compound listed in Table 12 are prepared analogously to the instructions of Example 27

TABLE 12

D—N(=O)—O—[ring]—NH—C(=O)—CH₃

| Ex. No. | D | Yield (% of theory) | Melting point (°C.) | R_f/mobile phase (ratio) | MS(FAB) m/z (M + H)+ |
|---|---|---|---|---|---|
| 84 | 6-methyl-pyridin-2-yl (H₃C) | 58 | 121 | 0.20 I (95:5) | 249[a] |
| 85 | 3-phenyl-pyridazin-6-yl | 86 | 200 | 0.54 I (9:1) | 313 |

[a] MS(EI) m/z = M+

The compounds listed in Tables 13 and 14 are prepared analogously to the instructions of Example 36

TABLE 13

| Ex. No. | R³⁶ | Yield (% of theory) | Melting point (°C.) | R_f/mobile phase (ratio) | MS(FAB) m/z (M + H)⁺ |
|---|---|---|---|---|---|
| 86 | 4-(CH₃CO)-C₆H₄- | 76 | 208 with decomp. | 0.21 I (100:5) | 353 |
| 87 | C₆H₅- | 93 | 202 with decomp. | 0.26 I (100:5) | 311 |
| 88 | 3-OHC-C₆H₄- | 88 | 194 with decomp. | 0.18 I (100:5) | 339 |
| 89 | 4-OHC-C₆H₄- | 91 | 172 with decomp. | 0.09 I (100:5) | 339 |
| 90 | 4-F-C₆H₄- | 99 | 205 with decomp. | 0.24 I (100:5) | 330 |
| 91 | 3-CHO-thien-2-yl | 75 | 195 with decomp. | 0.19 I (100:5) | 346 |
| 92 | 3-(CH₃CO)-C₆H₄- | 84 | 204 with decomp. | 0.23 I (100:5) | 353 |
| 93 | 4-CH₃-C₆H₄- | 96 | 203 with decomp. | 0.38 I (100:5) | 325 |
| 94 | 2-(CH₃CO)-thien-5-yl | 54 | >210 with decomp. | 0.25 I (100:5) | 359 |
| 95 | 3-O₂N-C₆H₄- | 66 | 204 | 0.29 I (100:5) | 356 |
| 96 | 4-Cl-C₆H₄- | 82 | 206 with decomp. | 0.34 I (100:5) | 345 |

TABLE 13-continued

[Structure: R³⁶-pyridinyl-N-C(=O)-O-CH-CH₂-NH-C(=O)-CH₃ oxazolidinone]

| Ex. No. | R³⁶ | Yield (% of theory) | Melting point (°C.) | R_f/mobile phase (ratio) | MS(FAB) m/z (M + H)⁺ |
|---|---|---|---|---|---|
| 97 | 3-Cl, 4-F-phenyl | 84 | 202 with decomp. | 0.2 I (100:5) | 363 |
| 98 | 4-CH₃O-phenyl | 92 | 190 with decomp. | 0.25 I (100:5) | 341 |
| 99 | 3-H₂N-phenyl | 79 | 191 with decomp. | 0.09 I (100:5) | 326 |
| 100 | 3-(H₃C-C(=O))-phenyl | 82 | 198 with decomp. | 0.27 I (100:5) | 367 |

TABLE 14

[Structure: R³⁷-quinolinyl-N-C(=O)-O-CH-CH₂-NH-C(=O)-CH₃ oxazolidinone]

| Ex. No. | R³⁷ | Yield (% of theory) | Melting point (°C.) | R_f/mobile phase (ratio) | MS(FAB) m/z (M + H)⁺ |
|---|---|---|---|---|---|
| 101 | 4-F-phenyl | 14 | 228 with decomp. | 0.5 I (100:5) | 380 |
| 102 | 4-OHC-phenyl | 64 | 159 with decomp. | 0.35 I (100:5) | 390 |
| 103 | 4-(CH₃-C(=O))-phenyl | 40 | 207 with decomp. | 0.21 I (100:5) | 404 |
| 104 | phenyl | 65 | 211 with decomp. | 0.45 I (100:5) | — |

TABLE 14-continued

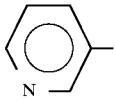

| Ex. No. | R[37] | Yield (% of theory) | Melting point (°C.) | R$_f$/mobile phase (ratio) | MS(FAB) m/z (M + H)$^+$ |
|---|---|---|---|---|---|
| 105 | (3-pyridyl) | 18 | 200 with decomp. | 0.4 I (100:5) | 362 |

Example 106

(5S)-3-[5(4-(Piperidin-1-yl)-phenyl)-pyridin-2-yl]-5-acetyl-aminomethyl-oxazolidin-2-one

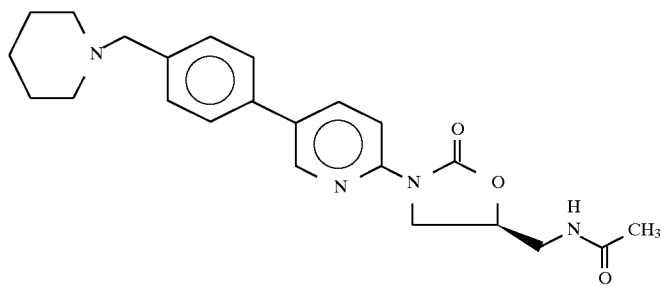

0.37 ml (1.26 mmol) of tetraisopropoxytitanium is added to a stirred suspension of 340 mg (1.00 mmol) of the aldehyde from Example 40 and 86 mg (1.00 mmol) of piperidine in 10 ml of methylene chloride and the mixture is stirred at room temperature for 1 hour, whereupon a clear solution forms. Thereafter, the solvent is evaporated off in vacuo, the residue is dissolved in 2 ml of ethanol, 44 mg (0.67 mmol) of sodium cyanoborohydride are added and the mixture is stirred at room temperature for 18 hours. The solvent is evaporated off in vacuo and the residue is taken up in 40 ml of a mixture of ethyl acetate and water 1:1. The organic phase is separated off, washed with 2×10 ml of water and 10 ml of NaCl solution and dried over MgSO$_4$. Evaporation of the solvent and chromatography of the residue over 80 g of silica gel (methylene chloride:methanol 9:1) gives 187 mg (46%) of the title compound as colourless crystals.

Melting point: 154°–155° C. R$_f$=0.20 (methylene chloride:methanol 9:1). MS (FAB) m/z=409 (M+H)$^+$. $^1$H-NMR (200 MHZ, D$_6$-DMSO); δ=1.3–1.6 (m, 6H, CH$_2$); 1.84 (s, 3H, COCH$_3$); 2.33 (m, 4H CH$_2$N); 3.45 (m, 4H, CH$_2$N); 3.91 (dd, I=8.10 N$_2$, 1H, H-4 trans); 4.25 (dd, I=10, 10 N$_2$, 1H, H-4 cis); 4.78 (m, 9H, H-5); 7.40, 7.68 (AB, I=9 H$_2$, aromatic H; 8.13 (s, 2H, pyridyl H-3,4); 8.25 (m, 1H, NHCO); 8.70 (m, 1H, pyridyl H-6).

As described for Example 106, the compounds listed in Table 15 are obtained as lyophilizates by reductive amination of the aldehyde from Example 40 and conversion into the corresponding hydrochlorides (analogously to Example 62):

TABLE 15

[Structure: 2HCl × R24R23N-CH2-phenyl-pyridinyl-N-oxazolidinone-CH2-NH-C(=O)-CH3]

| Ex. No. | R23 together with R24 or R23 and R24 | Yield [% of theory] | Rf/mobile phase (ratio) | MS(FAB m/z (M + H)+ |
|---|---|---|---|---|
| 107 | (cyclohexyl ring) | 41 | 0.11 I (9:1) | 408 |
| 108 | (morpholine, O-) | 39 | 0.49 I (9:1) | 410 a) |
| 109 | (cyclopropyl)—H | 20 | 0.15 I (9:1) | 380 a) |
| 110 | CH3N (piperazinyl) | 27 | 0.11 I (9:1) | 424 |
| 111 | (phenyl-piperazinyl) | 25 | 0.53 I (9:1) | 486 |
| 112 | (pyrimidinyl-piperazinyl) | 20 | 0.49 I (9:1) | 488 |

Example 113

(5 S)-3-[5-(4-Hydroximinomethyl)-phenyl)-pyridin-2-yl]-5-acetyl-aminomethyl-oxazolidin-2-one

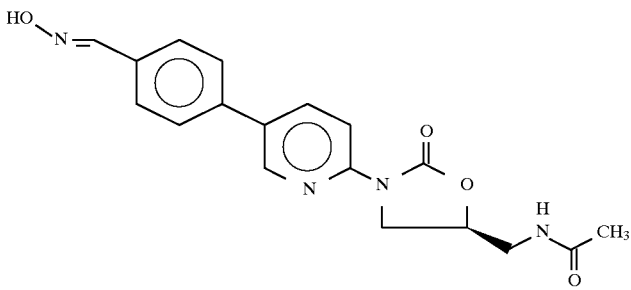

0.33 ml (4.00 mmol) of pyridine and 278 mg (4.00 mmol) of hydroxylaminehydrochloride are added to a stirred suspension of 340 mg (1.00 mmol) of the aldehyde from Example 40 in 15 ml of ethanol, and the mixture is heated under reflux for 1 hour. The mixture is allowed to cool, and 15 ml of water are added. The precipitate is separated off by filtration, washed several times with water and dried in vacuo over Sicapent. 173 mg of the title compound are obtained as colourless crystals.

Melting point: 233°–234° C. $R_f$=0.29 (methylene chloride:methanol 9:1). MS (DC1, $NH_3$) m/z=355 $(M+H)^+$.
$^1$H-NMR (250 MHZ, $D_6$-DMSO); δ=1.85 (s, 3H, $COCH_3$); 3.46 (m, 2H, $CH_2N$); 3.92 (dd, I=8, 10 Hz, 1H, H-4 trans); 4.27 (dd, I=10, 10 Hz, 1H, H-4 cis); 4.78 (m, 1H, H-5); 7.71, 7.79 (AB, I=11 Hz, 4H aromatic H); 8.20 (m, 2H, pyridyl H-3,4); 3,4); 8.26 (m, 1H, NHCO); 8.72 (bs, 1H, pyridyl H-6).

As described for Example 113, the compounds listed in Table 16 are obtained by condensation of the aldehyde from Example 40 with the corresponding . . . :

TABLE 16

[Structure: R^18—N=CH—C6H4—pyridin-2-yl—N(oxazolidinone with CH2NHC(O)CH3 side chain)]

| Ex. No. | R^18 | Yield [% of theory] | Melting point [°C.] | R$_f$/mobile phase (ratio) | MS(FAB) m/z (M + H)^+ |
|---|---|---|---|---|---|
| 114 | [benzyl-O-CH2-] | 90 | 206 | 0.14 I (9:1) | 444 |
| 115 | H2N-C(=O)-N(H)- | 81 | 275 | 0.15 I (9:1) | 397 |
| 116 | H2N-C(=S)-N(H)- | 92 | 272 | 0.35 I (9:1) | 413 |
| 117 | H2N-C(=NH)-N(H)- | 58 | 235 | 0.01 III (8:2) | 396 |
| 117^a) | pyridin-2-yl-CH2-N(H)-C(=NH)-N(H)- | 96 | 255 | 0.05 I (9:1) | 487 |

Example 118

(5S)-3-[5-(4-Formyl-phenyl)-pyridin-2-yl]-5-acetyl-aminomethyl-oxazolidin-2-one bisulphite adduct

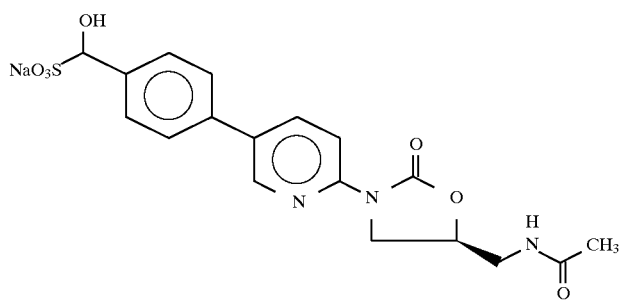

A stirred mixture of 232 mg (0.50 mmol) of the aldehyde from Example 40 and 0.2 ml of 39% strength aqueous NaHSO$_3$ solution in 20 ml of ethanol is heated under reflux. After cooling, the precipitate is separated off by filtration, washed with ethanol and dried in vacuo over Sicapent. 225 mg (98%) of the title compound are obtained as colourless crystals.

Melting point: >310° C. R$_f$=0.29 (methylene chloride:methanol 9:1). MS (FAB) m/z =420 (M)^+. $^1$H-NMR (200 MHZ, D$_6$-DMSO); δ=1.90 (s, 3H, COCH$_3$); 3.48 (m, 2H, NCH$_2$); 3.92 (dd, I=8, 10 Hz, 1H, H-4 trans); 4.26 (dd, I=10, 10 Hz, 1H, H-4 cis); 4.75 (m, 1H, H-5); 5.01, (d, I=5 Hz, 1H, CHOH); 5.92 (d, 5 Hz, 1H, CHOH); 7.57 (m, 2H, aromatic H); 8.18 (s, 2H, pyridyl H-3,4); 8.30 (m, 1H, NHCO); 8.70, (s, 1H, pyridyl H-6).

Example 119

(5S)-3-[5-((4-(-n-Butyloxycarbonyl-phenyl)-aminocarbonyl)oxymethyl)-phenyl)-pyridin-2-yl]-5-acetyl-aminomethyl-oxazolidin-2-one

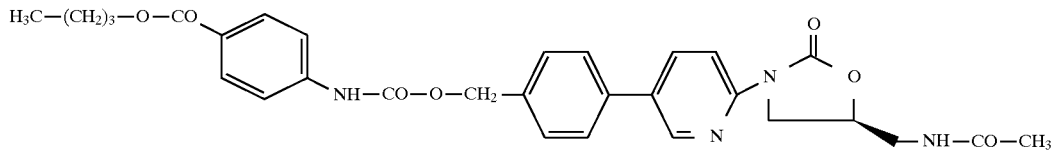

0.11 ml (0.77 mmol) of triethylamine and 61 mg (0.28 mmol) of n-butyl 4-isocyanatobenzoate are added to a stirred solution of 80 mg (0.25 mmol) of the alcohol from Example 120 in 35 ml of methylene chloride, whereupon a voluminous precipitate is formed. The mixture is subsequently stirred at room temperature for 1 hour and the precipitate is separated off by filtration, washed with 3×5 ml of methylene chloride and dried under a high vacuum over Sicapent. 82 mg (77%) of the title compound are obtained as colourless crystals.

Melting point: 233°–234° C. $R_f$=0.43 (methylene chloride:methanol 9:1). MS (DCI, $NH_3$) m/z=561 (M+H)$^+$. $^1$H-NMR (200 MHZ, $D_6$-DMSO); δ=0.93 (t, I=6.5 Hz, 3H, $CH_3$); 1.40 (m, 2H, $CH_2$); 1.70 (m, 2H, $CH_2$), 1.82 (s, 3H, $COCH_3$); 3.46 (m, 2H, $CH_2N$); 3.92 (dd, I=8, 10 Hz, 1H, H-3 trans); 4.25 (m, 3H, 4 cis, $CH_2OCO$); 4.75 (m, 1H, H-5); 5.25 (2, 2H, $CH_2O$); 7.55, 7.61, 7.77, 7.90 (AB, I 10 Hz, 8H, $C_6NH_4$); 8.18 (s, 2H, pyridyl H-3,4); 8.28 (m, 1H, NHCO); 8.73 (s, 1H, pyridyl H-6); 10.23 (s, 1H, NHCOO).

The compounds listed in Table 17 were prepared analogously to the examples described above:

TABLE 17

| Ex. No. | $R^{38}$ | Preparation method analogous to Example | Yield [% of theory] | Melting point [°C.] | $R_f$/mobile phase (ratio) | MS(FAB) m/z (M + H)$^+$ |
|---|---|---|---|---|---|---|
| 120 | HO—$CH_2$— | 60 | 81 | 175 | 0.29 I (9:1) | 342 |
| 121 | $CH_3SO_2O$—$CH_2$— | 15 | 86 | 168 | 0.42 I (9:1) | 420 |
| 122 | $N_3$—$CH_2$— | 19 | 59 | 142 | 0.46 I (9:1) | 367 |
| 123 | 2 HCl × $H_2N$—$CH_2$— | 23 | 46 |  | 0.02 I (9:1) | 341 |
| 124 | $CH_3CONH$—$CH_2$— | 27 | 68 | 215 | 0.24 I (9:1) | 383 |
| 125 | CHONH—$CH_2$— | 27 |  |  |  |  |
| 126 | $CH_3$—C$_6$H$_4$—$SO_2NH$—$CH_2$— | 15 | 76 | amorphous | 0.32 I (9:1) | 495 |

Example 127

(5 S)-3-[5-(4-Dimethoxyphosphorylamino-methyl)-phenyl)-pyridin-2-yl]-5-acetylaminomethyl-oxazolidin-2-one

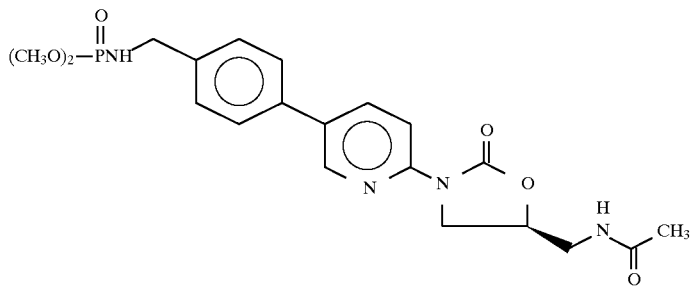

A stirred solution of 310 mg (0.85 mmol) of the azide from Example 122 in 1.5 ml of dimethoxymethane is heated to 70° C. and 0.12 ml (1.02 mmol) of trimethyl phosphite is slowly added dropwise (evolution of gas!). Thereafter, the mixture is stirred at 70° C. for 2 hours, allowed to cool and poured into 30 ml of ethyl acetate:water 1:1. The organic phase is separated off and dried over MgSO$_4$. Evaporation of the solvent and chromatography of the residue over 15 g of silica gel (methylene chloride:methanol 97:3) gives 213 mg (56%) of the title compound as colourless crystals.

Melting point: 131°–132° C. R$_f$=0.28 (Methylene chloride:methanol 9:1)

The hydrochlorides listed in Table 18 were obtained as described for Example 62.

TABLE 18

| Ex. No. | D | Yield [% of theory] | Melting point [°C.] | R$_f$/mobile phase (ratio) | MS(FAB) m/z (M + H)$^+$ |
|---|---|---|---|---|---|
| 128 |  | 90 | 211 | 0.67 III (8:2) | 365 |
| 129 | 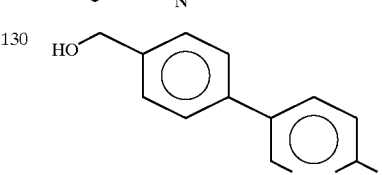 | 81 | Lyophilizate | 0.58 II (9:1) | 287 |
| 130 | 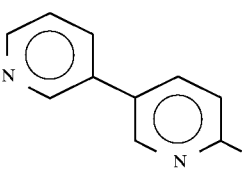 | 86 | Lyophilizate | 0.30 I (9:1) | — |
| 131 |  | 82 | Lyophilizate | 0.32 I (9:1) | 313 |

Example 132

(5 S)-3-[5-(4-Methyl-1H-tetrazol-5-yl-thiomethyl)-phenyl)-pyridin-2-yl]-5-acetylaminomethyl-oxazolidin-2-one

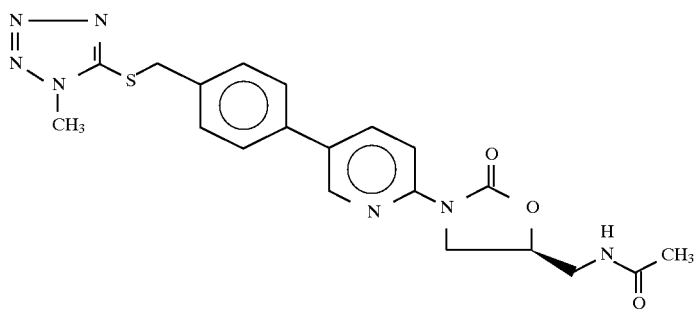

0.05 ml (0.32 mmol) of triethylamine and 36 mg (0.31 mmol) of 1-methyltetrazole-5-thiol are added to a solution of 122 mg (0.29 mmol) of the mesylate from Example 121 in 2 ml of acetonitrile and the mixture is stirred at room temperature for 1 hour. Thereafter, 1 g of silica gel is added, the solvent is evaporated off in vacuo and the residue is purified by chromatography over 10 g of silica gel (ethyl acetate).

72 mg (57%) of the title compound are obtained as colourless crystals. Melting point: 154°–155° C. $R_f$=0.10 (ethyl acetate). MS (DCI, $NH_3$) m/z=440 (M+H)$^+$. $^1$H-NMR (300 MHz, $D_6$-DMSO); δ=1.85 (s, 3H, $COCH_3$); 3.45 (m, 2H, $CH_2N$); 3.89 (s, 3H, $NCH_3$); 3.91 (m, 1H, H-4 trans); 4.26 (dd, I. 10, 10 Hz, 1H, H-4 cis); 4.58 (s, 2H, $CH_2$); 4.77 (m, 1H, H-5); 7.50, 7.68 (AB, I=9 Hz, 4H, Harom); 8.16 (s, 2H, pyridyl H-3,4); 8.25 (m, 1H, NHCO); 8.70 (s, 1H, pyridyl H-6).

As described in Example 132, the compounds listed in Table 19 were obtained by reaction of the mesylate with the corresponding heteroarylthiols.

TABLE 19

R$^{25}$S—[structure: benzyl-phenyl-pyridyl-N-acyl-oxazolidinone-CH$_2$-NHC(O)CH$_3$]

| Ex. No. | R$^{25}$ | Yield [% of theory] | Melting point [°C.] | $R_f$/mobile phase (ratio) | MS(FAB) m/z (M + H)$^+$ |
|---|---|---|---|---|---|
| 133 | 1-methylbenzimidazol-2-yl | 60 | 172 | 0.15 IV | 488 |
| 134 | 1-phenylimidazol-2-yl | 40 | 101 | 0.40 I (95:5) | |
| 135 | 5-tert-butyl-1,3,4-thiadiazol-2-yl | 55 | 164 | 0.15 IV | 498 |

As described for Example 65, the N-oxides listed in Table 20 are obtained.

TABLE 20

| Ex. No. | D | Yield | Start material from Example | Melting point [°C.] | $R_f$/mobile phase (ratio) | MS(FAB) m/z (M + H)+ |
|---|---|---|---|---|---|---|
| 136 | 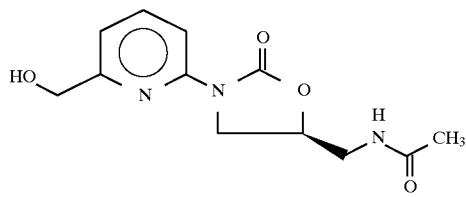 | 83 | 49 | 173 | 0,06 I(9:1) | 266 |

Example 137

(5S)-3-[6-(Hydroxymethyl)-pyridin-2-yl]-5-acetyl-aminomethyl-oxazolidin-2-one 18.50 ml (131.00 mmol) of trifluoroacetic anhydride are added to a stirred solution, cooled to 0° C., of 5.80 g (21.88 mmol) of the N-oxide from Example 138 in 50 ml of anhydrous DMF in the course of 6 minutes. Thereafter, the cooling bath is removed and the mixture is subsequently stirred at room temperature for 1 hour. The reaction mixture is then stirred into 130 ml of ice-cold saturated $Na_2CO_3$ solution and the mixture is stirred thoroughly for 1 hour, during which it is allowed to warm to room temperature. The aqueous phase is extracted with 50 ml of ethyl acetate (8×) and with 50 ml of methylene chloride (5×) and the combined extracts are dried over $MgSO_4$. Evaporation of the solvent in vacuo and chromatography of the residue over 100 g of silica gel (methylene chloride:methanol 9:1) gives 5.79 g (98%) of the title compound as pale yellow crystals.

Melting point: 138° C. $R_f$=0.26 (methylene chloride:methanol 9:1). MS (DCI, $NH_3$)m/z=266 (M+H)$^+$. $^1$H-NMR (200 MHz, $D_6$-DMSO); δ=1.84 (s, 3H, $COCH_3$); 3.43 (m, 2H, $CH_2N$); 3.82 (dd, I=8, 10 Hz, IH, H-4trans), 4.20 (dd I=10, 20, IH, H-4 cis); 4.50 (d, I=6 Hz, 2H, $CH_2OH$); 4.72 (m, 1H, H-5); 5.42 (t, I=6 Hz, 1H, $CH_2OH$); 7.21 (d, I=8 Hz, 1H, pyridyl-H); 7.90 (m, 2H, pyridyl-H); 8.25 (bt, I=7 Hz, 1H, NHCO).

We claim:

1. A heteroaryl-oxazolidinone of the formula (I):

(I)

in which

R$^1$ represents —NH$_2$ or —NHCOR$^6$; and
in which
R$^6$ represents hydrogen or straight-chain or branched alkyl having 1 to 8 carbon atoms; and D represents pyridyl, which is optionally substituted by alkyl having 1 to 6 carbon atoms, or by phenyl or pyridyl, both of which are optionally substituted by alkyl having 1 to 6 carbon atoms, formyl, or alkanoyl having 1 to 6 carbon atoms;

or a salt thereof.

2. A compound according to claim 1, in which

R$^1$ represents —NHCOR$^6$; and
in which
R$^6$ represents hydrogen or straight-chain or branched alkyl having 1 to 4 carbon atoms; and D represents pyridyl, which is optionally substituted by alkyl having 1 to 6 carbon atoms, or by phenyl or pyridyl, both of which are optionally substituted by alkyl having 1 to 4 carbon atoms, formyl, or alkanoyl having 1 to 4 carbon atoms;

or a salt thereof.

3. A compound according to claim 1, which is the hydrochloride salt of a compound selected from the group consisting of

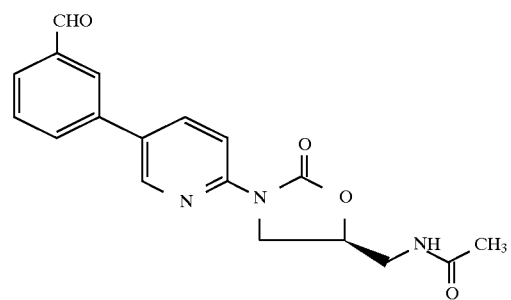
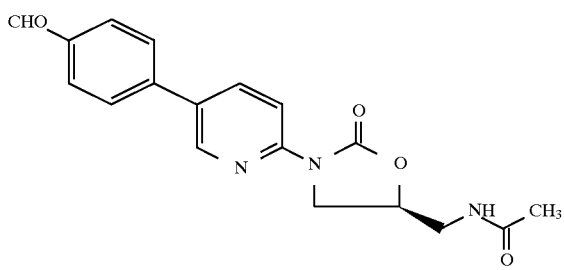
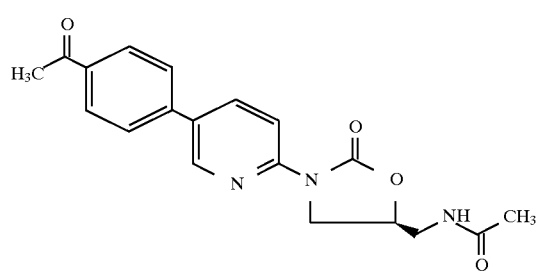
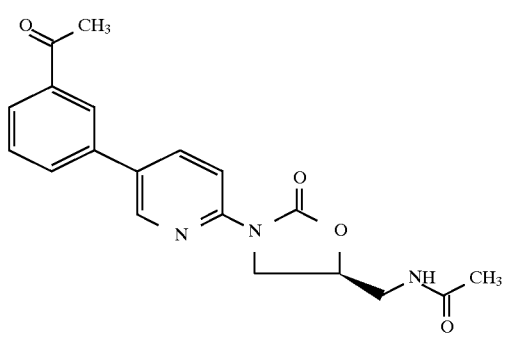
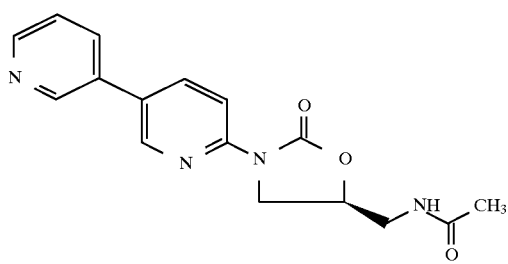
4. A compound according to claim 1, which has the formula
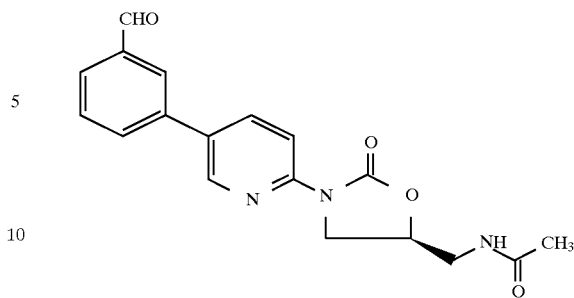
or a salt thereof.
5. A compound according to claim 1, which has the formula
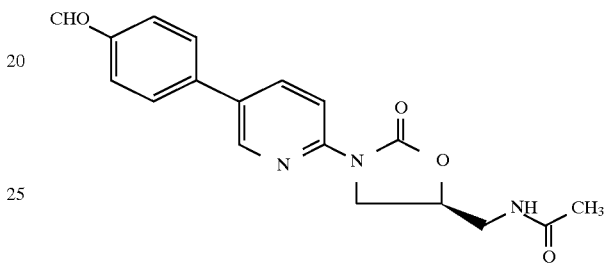
or a salt thereof.
6. A compound according to claim 1, which has the formula
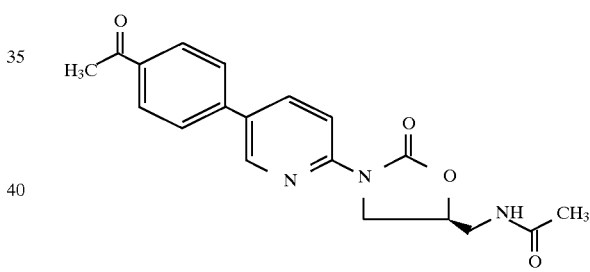
or a salt thereof.
7. A compound according to claim 1, which has the formula
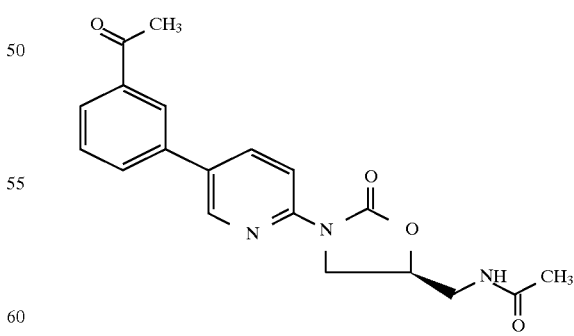
or a salt thereof.
8. A compound according to claim 1 which has the formula

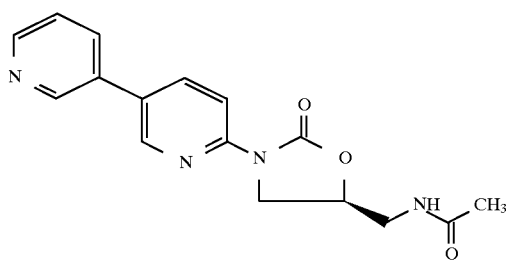

or a salt thereof.

9. The compound according to claim 1, wherein the salt of the compound is the hydrochloride salt.

10. A pharmaceutical composition which comprises of a heteroaryl-oxazolidinone or salt thereof according to claim 1, and an inert carrier.

11. A pharmaceutical composition according to claim 10, wherein the compound is of the formula

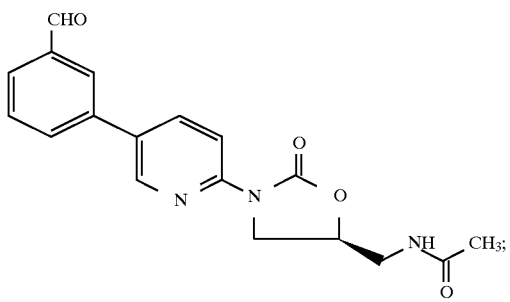

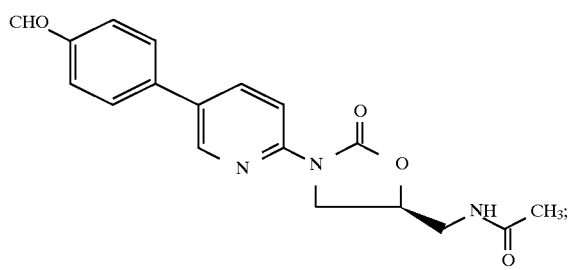

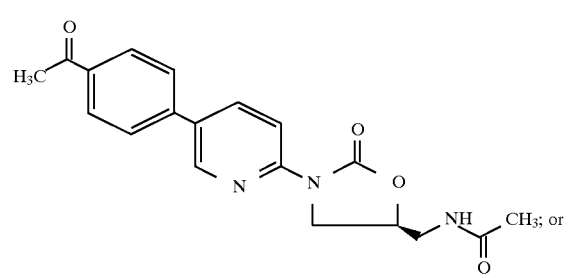

-continued

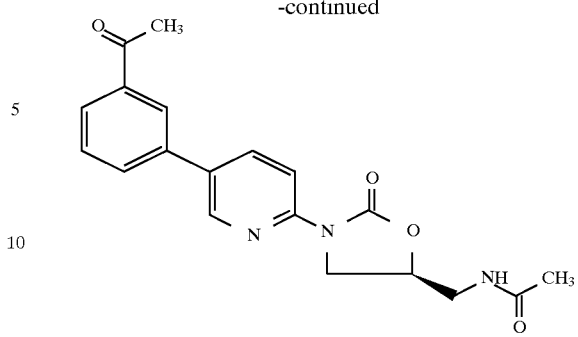

or a salt thereof.

12. The pharmaceutical composition according to claim 10, wherein the compound is

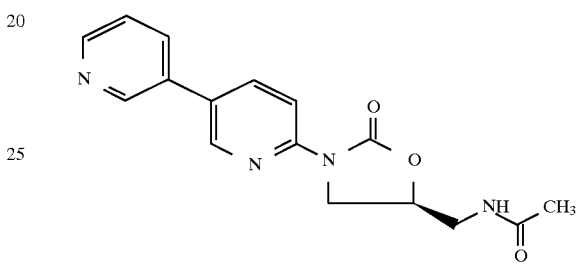

or a salt thereof.

13. The pharmaceutical composition according to claim 12, wherein the salt is a hydrochloride salt.

14. A method of treating bacterial infections to a host in need thereof which comprises administering antibacterially of a heteroaryl-oxazolidinone or a salt thereof according to claim 1 to said host.

15. The method according to claim 14, wherein the heteroaryl-oxazolidinone is of the formula

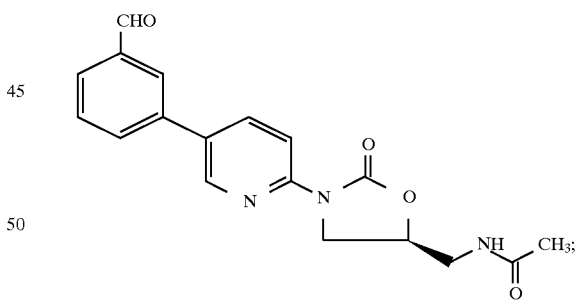

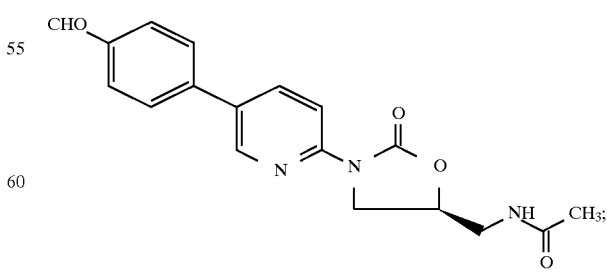

-continued
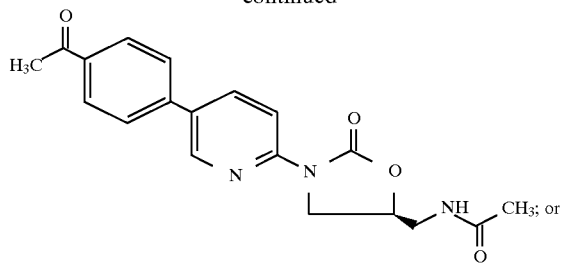
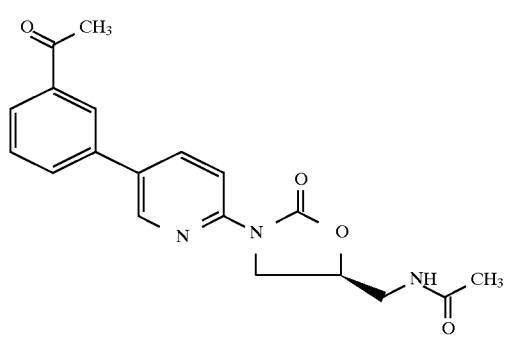
or a salt thereof.
16. The method according to claim 14, wherein the compound is
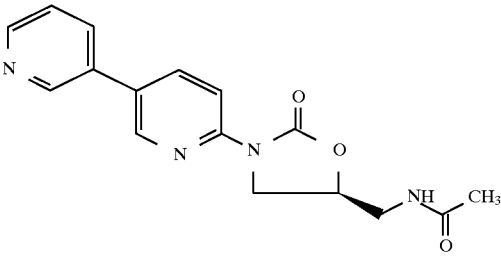
or a salt thereof.
17. The method according to claim 16, wherein the salt of the compound is the hydrochloride salt.
* * * * *

UNITED STATES PATENT AND TRADEMARK OFFICE
CERTIFICATE OF CORRECTION

PATENT NO : 5,843,967
DATED : December 1, 1998
INVENTOR(S): Bernd Riedl, et al.

It is certified that error appears in the above-identified patent and that said Letters Patent is hereby corrected as shown below:

Col. 76, Line 36    Delete "antibacterially" and Substitute --an antibacterially effective amount--

Signed and Sealed this

Twenty-second Day of February, 2000

Attest:

Q. TODD DICKINSON

*Attesting Officer*    *Commissioner of Patents and Trademarks*